US012678273B2

(12) United States Patent
Sneider

(10) Patent No.: US 12,678,273 B2
(45) Date of Patent: Jul. 14, 2026

(54) IMPLANTABLE PROTHESIS FOR MINIMALLY INVASIVE HERNIA REPAIR

(71) Applicant: Covidien LP, Mansfield, MA (US)

(72) Inventor: Mark S. Sneider, Minnetonka, MN (US)

(73) Assignee: Covidien LP, Mansfield, MA (US)

( * ) Notice: Subject to any disclaimer, the term of this patent is extended or adjusted under 35 U.S.C. 154(b) by 173 days.

(21) Appl. No.: 18/777,483

(22) Filed: Jul. 18, 2024

(65) Prior Publication Data

US 2024/0366356 A1 Nov. 7, 2024

Related U.S. Application Data

(63) Continuation of application No. 17/238,975, filed on Apr. 23, 2021, now Pat. No. 12,064,330.

(60) Provisional application No. 63/016,750, filed on Apr. 28, 2020.

(51) Int. Cl.
*A61F 2/00* (2006.01)
(52) U.S. Cl.
CPC .... *A61F 2/0063* (2013.01); *A61F 2220/0016* (2013.01)
(58) Field of Classification Search
CPC ........... A61B 17/00234; A61B 17/0057; A61F 2/0063; A61F 2210/0004; A61F 2220/0016; A61F 2002/0068; A61F 2002/30467; A61F 2220/0025; A61F 2220/0083; A61F 2230/0063
See application file for complete search history.

(56) References Cited

U.S. PATENT DOCUMENTS

| 1,187,158 | A | 6/1916 | Mcginley |
|---|---|---|---|
| 3,054,406 | A | 9/1962 | Usher |
| 3,118,294 | A | 1/1964 | Van Laethem |
| 3,124,136 | A | 3/1964 | Usher |
| 3,272,204 | A | 9/1966 | Artandi et al. |
| 3,276,448 | A | 10/1966 | Kronenthal |
| 3,320,649 | A | 5/1967 | Naimer |
| 3,364,200 | A | 1/1968 | Ashton et al. |
| 3,570,482 | A | 3/1971 | Shigeru et al. |
| 3,718,725 | A | 2/1973 | Hamano |
| 4,006,747 | A | 2/1977 | Kronenthal et al. |
| 4,060,081 | A | 11/1977 | Yannas et al. |

(Continued)

FOREIGN PATENT DOCUMENTS

| CA | 1317836 C | 5/1993 |
|---|---|---|
| CN | 201879864 U | 6/2011 |

(Continued)

OTHER PUBLICATIONS

Amid, P., "Lichtenstein tension-free hernioplasty: Its inception, evolution, and principles," Hernia, 2004; pp. 1-7, 8, published online Sep. 2003.

(Continued)

*Primary Examiner* — Katherine M Shi
(74) *Attorney, Agent, or Firm* — Weber Rosselli & Cannon LLP

(57) ABSTRACT

An implantable prosthesis for hernia repair is designed for minimally invasive, robotic, or laparoscopic surgery. Various embodiments of the implantable prosthesis are tailored for inguinal hernia repair, including direct, indirect, and bilateral hernia defects, as well as for femoral hernia repair.

19 Claims, 11 Drawing Sheets

(56)                References Cited

U.S. PATENT DOCUMENTS

| | | | |
|---|---|---|---|
| 4,173,131 A | 11/1979 | Melton et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,840,629 A | 6/1989 | Bustos |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,071,433 A | 12/1991 | Naestoft et al. |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | Mcmurray |
| 5,350,583 A | 9/1994 | Yoshizato et al. |
| 5,356,432 A | 10/1994 | Rutkow et al. |
| 5,368,549 A | 11/1994 | Mcvicker |
| 5,368,602 A | 11/1994 | Torre |
| 5,370,650 A | 12/1994 | Jonathan et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,456,720 A | 10/1995 | Schultz et al. |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,584,884 A | 12/1996 | Pignataro |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | Mcgregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,954,767 A | 9/1999 | Pajotin et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |

(56)     References Cited

U.S. PATENT DOCUMENTS

| | | | |
|---|---|---|---|
| 6,015,844 A | 1/2000 | Harvey et al. |
| 6,039,686 A | 3/2000 | Robert |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D Aversa et al. |
| 6,113,623 A | 9/2000 | Sgro |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Robert |
| 6,334,872 B1 | 1/2002 | Termin et al. |
| 6,368,541 B1 | 4/2002 | Pajotin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Mueller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,666,893 B2 | 12/2003 | Burg et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Bryan et al. |
| 6,723,133 B1 | 4/2004 | Pajotin |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,740,122 B1 | 5/2004 | Pajotin |
| 6,743,435 B2 | 6/2004 | Devore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |

(56)  References Cited

U.S. PATENT DOCUMENTS

| | | | |
|---|---|---|---|
| 7,041,868 B2 | 5/2006 | Greene et al. |
| 7,060,103 B2 | 6/2006 | Carr et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,213,421 B2 | 5/2007 | Shirasaki et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,235,504 B2 | 6/2007 | Shirasaki et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,476,249 B2 | 1/2009 | Frank |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,372 B2 | 3/2010 | Shfaram et al. |
| 7,670,380 B2 | 3/2010 | Cauthen, III et al. |
| 7,682,381 B2 | 3/2010 | Rakos et al. |
| 7,709,017 B2 | 5/2010 | Tayot et al. |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,875,074 B2 | 1/2011 | Chen et al. |
| 7,900,484 B2 | 3/2011 | Cherok et al. |
| 7,931,695 B2 | 4/2011 | Ringeisen |
| 7,998,152 B2 | 8/2011 | Frank |
| 8,007,531 B2 | 8/2011 | Frank |
| 8,016,841 B2 | 9/2011 | Magnusson et al. |
| 8,052,759 B2 | 11/2011 | Dupic et al. |
| 8,079,023 B2 | 12/2011 | Chen |
| 8,100,924 B2 | 1/2012 | Browning |
| 8,101,116 B2 | 1/2012 | Lindh, Sr. et al. |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,198,087 B2 | 6/2012 | Bayon et al. |
| 8,206,632 B2 | 6/2012 | Rousseau et al. |
| 8,215,310 B2 | 7/2012 | Browning |
| 8,313,499 B2 | 11/2012 | Magnusson et al. |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,388,633 B2 | 3/2013 | Rousseau et al. |
| 8,435,307 B2 | 5/2013 | Paul |
| 8,470,355 B2 | 6/2013 | Skalla et al. |
| 8,506,627 B2 | 8/2013 | Van et al. |
| 8,562,633 B2 | 10/2013 | Cully et al. |
| 8,574,627 B2 | 11/2013 | Martakos et al. |
| 8,591,534 B2 | 11/2013 | Rousseau et al. |
| 8,603,117 B2 | 12/2013 | Zoland et al. |
| 8,709,094 B2 | 4/2014 | Stad et al. |
| 8,728,159 B2 | 5/2014 | Kim et al. |
| 8,734,471 B2 | 5/2014 | Deitch |
| 8,746,014 B2 | 6/2014 | Mortarino |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,578 B2 | 9/2014 | Bayon et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,888,863 B2 | 11/2014 | Walther et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 8,986,377 B2 | 3/2015 | Richter et al. |
| 9,034,357 B2 | 5/2015 | Stopek |
| 9,113,993 B2 | 8/2015 | Lee |
| 9,119,898 B2 | 9/2015 | Bayon et al. |
| 9,211,175 B2 | 12/2015 | Stopek et al. |
| 9,216,075 B2 | 12/2015 | Bailly et al. |
| 9,308,068 B2 | 4/2016 | Spinnler et al. |
| 9,457,129 B2 | 10/2016 | Buevich et al. |
| 9,532,867 B2 | 1/2017 | Felix et al. |
| 9,549,812 B2 | 1/2017 | Shetty et al. |
| 9,585,744 B2 | 3/2017 | Moses et al. |
| 9,636,211 B2 | 5/2017 | Felix et al. |
| 9,650,730 B2 | 5/2017 | Heipl et al. |
| 9,655,715 B2 | 5/2017 | Limem et al. |
| 9,713,519 B2 | 7/2017 | Horton et al. |
| 9,750,595 B2 | 9/2017 | Thomas et al. |
| 9,801,704 B2 | 10/2017 | Bailly et al. |
| D803,401 S | 11/2017 | Limem et al. |
| 9,833,546 B2 | 12/2017 | Francois et al. |
| 9,839,507 B2 | 12/2017 | Harms et al. |
| D816,220 S | 4/2018 | Limem et al. |
| D816,221 S | 4/2018 | Limem et al. |
| 9,931,198 B2 | 4/2018 | Doucet et al. |
| 9,987,114 B2 | 6/2018 | Criscuolo et al. |
| 10,028,818 B2 | 7/2018 | Felix et al. |
| 10,058,417 B2 | 8/2018 | Limem et al. |
| D836,778 S | 12/2018 | Limem et al. |
| 10,159,552 B2 | 12/2018 | Trupiano et al. |
| 10,335,257 B2 | 7/2019 | Rizk et al. |
| 10,350,045 B2 | 7/2019 | Sun et al. |
| 10,357,350 B2 | 7/2019 | Astani-Matthies et al. |
| 10,398,542 B2 | 9/2019 | Griffin et al. |
| 10,532,127 B2 | 1/2020 | Limem et al. |
| 10,561,484 B2 | 2/2020 | Tao et al. |
| 10,568,728 B2 | 2/2020 | Felix et al. |
| 10,595,986 B2 | 3/2020 | Rehnke |
| 10,660,741 B2 | 5/2020 | Doucet et al. |
| 10,675,137 B2 | 6/2020 | Bailly et al. |
| 10,695,165 B2 | 6/2020 | Shetty et al. |
| D889,654 S | 7/2020 | Limem et al. |
| D889,655 S | 7/2020 | Limem et al. |
| 10,722,336 B2 | 7/2020 | Mathisen et al. |
| 10,722,345 B2 | 7/2020 | Limem et al. |
| D892,329 S | 8/2020 | Limem et al. |
| 10,765,507 B2 | 9/2020 | Moses et al. |
| 10,820,980 B2 | 11/2020 | Criscuolo et al. |
| 10,835,370 B2 | 11/2020 | Bowley et al. |
| 10,842,612 B2 | 11/2020 | Barere et al. |
| 10,874,498 B2 | 12/2020 | Rizk et al. |
| 10,926,003 B2 | 2/2021 | Stevenson et al. |
| 11,000,280 B2 | 5/2021 | Tannhauser et al. |
| 11,007,044 B2 | 5/2021 | Trupiano et al. |
| D927,689 S | 8/2021 | Limem et al. |
| 2002/0087174 A1 | 7/2002 | Capello |
| 2002/0095218 A1 | 7/2002 | Carr et al. |
| 2003/0086975 A1 | 5/2003 | Ringeisen |
| 2003/0106346 A1 | 6/2003 | Matsumoto |
| 2003/0114937 A1 | 6/2003 | Leatherbury et al. |
| 2003/0133967 A1 | 7/2003 | Ruszczak et al. |
| 2003/0181988 A1 | 9/2003 | Rousseau |

(56)     References Cited

U.S. PATENT DOCUMENTS

| | | |
|---|---|---|
| 2003/0187516 A1 | 10/2003 | Amid et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0036266 A1 | 2/2006 | Sulamanidze et al. |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | Mcalexander et al. |
| 2007/0129736 A1 | 6/2007 | Solecki |
| 2007/0198040 A1 | 8/2007 | Buevich et al. |
| 2007/0276178 A1 | 11/2007 | Carteron et al. |
| 2007/0276487 A1 | 11/2007 | Carteron et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0147200 A1 | 6/2008 | Rousseau et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0082864 A1 | 3/2009 | Chen et al. |
| 2009/0105526 A1 | 4/2009 | Piroli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0240288 A1 | 9/2009 | Guetty |
| 2009/0240342 A1 | 9/2009 | Lindh et al. |
| 2009/0270999 A1 | 10/2009 | Brown |
| 2009/0281558 A1 | 11/2009 | Li et al. |
| 2009/0318752 A1 | 12/2009 | Evans et al. |
| 2010/0104608 A1 | 4/2010 | Abuzaina et al. |
| 2010/0137679 A1 | 6/2010 | Lashinski et al. |
| 2010/0233421 A1 | 9/2010 | Lind et al. |
| 2010/0318108 A1 | 12/2010 | Datta et al. |
| 2011/0015760 A1 | 1/2011 | Kullas |
| 2011/0022171 A1 | 1/2011 | Richter et al. |
| 2011/0054604 A1 | 3/2011 | Becker |
| 2011/0144667 A1 | 6/2011 | Horton et al. |
| 2011/0188706 A1 | 8/2011 | Zhou |
| 2011/0190795 A1 | 8/2011 | Hotter et al. |
| 2011/0238094 A1 | 9/2011 | Thomas et al. |
| 2011/0251699 A1 | 10/2011 | Ladet et al. |
| 2011/0257666 A1 | 10/2011 | Ladet et al. |
| 2011/0257761 A1 | 10/2011 | Mortarino |
| 2012/0004723 A1 | 1/2012 | Mortarino et al. |
| 2012/0016388 A1 | 1/2012 | Houard et al. |
| 2012/0029537 A1 | 2/2012 | Mortarino |
| 2012/0053690 A1 | 3/2012 | Frank |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |

| | | |
|---|---|---|
| 2012/0179175 A1 | 7/2012 | Hammell et al. |
| 2012/0179176 A1 | 7/2012 | Wilson et al. |
| 2012/0197415 A1 | 8/2012 | Montanari et al. |
| 2012/0226352 A1 | 9/2012 | Becker |
| 2012/0232334 A1 | 9/2012 | Bell et al. |
| 2012/0283826 A1 | 11/2012 | Moses et al. |
| 2013/0103060 A1* | 4/2013 | Stopek .................. A61F 2/0063 |
| | | 606/151 |
| 2013/0178875 A1 | 7/2013 | Horton et al. |
| 2013/0204277 A1 | 8/2013 | Fabry et al. |
| 2013/0253645 A1 | 9/2013 | Kerr et al. |
| 2013/0296897 A1 | 11/2013 | Trupiano et al. |
| 2014/0044861 A1 | 2/2014 | Boey et al. |
| 2014/0100656 A1 | 4/2014 | Namnoum et al. |
| 2014/0148827 A1 | 5/2014 | Odermatt et al. |
| 2014/0222161 A1 | 8/2014 | Mathisen et al. |
| 2014/0276993 A1 | 9/2014 | Reilly et al. |
| 2014/0364684 A1 | 12/2014 | Lecuivre et al. |
| 2015/0142023 A1 | 5/2015 | Tannhauser et al. |
| 2015/0182670 A1 | 7/2015 | Rizk et al. |
| 2015/0250574 A1 | 9/2015 | Egnelov |
| 2015/0351899 A1 | 12/2015 | Mortarino |
| 2016/0193026 A1 | 7/2016 | Mortarino et al. |
| 2016/0213456 A1 | 7/2016 | Mortarino |
| 2016/0213457 A1 | 7/2016 | Mortarino |
| 2016/0237228 A1 | 8/2016 | Serrero et al. |
| 2016/0242899 A1 | 8/2016 | Lee et al. |
| 2017/0027678 A1 | 2/2017 | Skott et al. |
| 2017/0216009 A1 | 8/2017 | Felix et al. |
| 2017/0265990 A1 | 9/2017 | Martin et al. |
| 2018/0168804 A1 | 6/2018 | Nguyen et al. |
| 2018/0318057 A1 | 11/2018 | Bailly et al. |
| 2018/0325518 A1 | 11/2018 | Tannhauser et al. |
| 2019/0069983 A1 | 3/2019 | Rizk et al. |
| 2019/0117363 A1 | 4/2019 | Felix et al. |
| 2019/0247180 A1 | 8/2019 | Limem et al. |
| 2019/0254807 A1 | 8/2019 | Limem et al. |
| 2019/0269817 A1 | 9/2019 | Williams et al. |
| 2021/0052772 A1 | 2/2021 | Vermet et al. |
| 2021/0156080 A1 | 5/2021 | Lau et al. |
| 2023/0301766 A1 | 9/2023 | Bailly et al. |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 0544485 A1 | 6/1993 |
| EP | 0552576 A1 | 7/1993 |
| EP | 0611561 A1 | 8/1994 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 0827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 0898944 A2 | 3/1999 |
| EP | 1017415 A1 | 7/2000 |
| EP | 1036545 A2 | 9/2000 |
| EP | 1052319 A1 | 11/2000 |

(56) References Cited

FOREIGN PATENT DOCUMENTS

| EP | 1055757 | A1 | 11/2000 |
|----|---------|----|---------|
| EP | 1090590 | A2 | 4/2001 |
| EP | 1216717 | A1 | 6/2002 |
| EP | 1216718 | A1 | 6/2002 |
| EP | 0693523 | B1 | 11/2002 |
| EP | 1273312 | A2 | 1/2003 |
| EP | 1315468 | A2 | 6/2003 |
| EP | 1382728 | A1 | 1/2004 |
| EP | 1484070 | A1 | 12/2004 |
| EP | 1561480 | A2 | 8/2005 |
| EP | 1645232 | A1 | 4/2006 |
| EP | 1674048 | A1 | 6/2006 |
| EP | 1691606 | A1 | 8/2006 |
| EP | 1782848 | A2 | 5/2007 |
| EP | 2229918 | A1 | 9/2010 |
| EP | 3398554 | A1 | 11/2018 |
| FR | 2244853 | A1 | 4/1975 |
| FR | 2257262 | A1 | 8/1975 |
| FR | 2308349 | A1 | 11/1976 |
| FR | 2453231 | A1 | 10/1980 |
| FR | 2612392 | A1 | 9/1988 |
| FR | 2682284 | A1 | 4/1993 |
| FR | 2715309 | A1 | 7/1995 |
| FR | 2715405 | A1 | 7/1995 |
| FR | 2724563 | A1 | 3/1996 |
| FR | 2730406 | A1 | 8/1996 |
| FR | 2744906 | A1 | 8/1997 |
| FR | 2766698 | A1 | 2/1999 |
| FR | 2771622 | A1 | 6/1999 |
| FR | 2773057 | A1 | 7/1999 |
| FR | 2774277 | A1 | 8/1999 |
| FR | 2779937 | A1 | 12/1999 |
| FR | 2859624 | B1 | 12/2005 |
| FR | 2876020 | A1 | 4/2006 |
| FR | 2863277 | B1 | 6/2006 |
| FR | 2884706 | B1 | 4/2008 |
| FR | 2929834 | A1 | 10/2009 |
| FR | 2953709 | A1 | 6/2011 |
| GB | 1174814 | A | 12/1969 |
| GB | 2051153 | A | 1/1981 |
| GB | 2306110 | A | 4/1997 |
| JP | H0332677 | U | 3/1991 |
| JP | H05237128 | A | 9/1993 |
| JP | H09137380 | A | 5/1997 |
| JP | H11146888 | A | 6/1999 |
| JP | 2008538300 | A | 10/2008 |
| JP | 2011078767 | A | 4/2011 |
| NZ | 563828 | A | 9/2011 |
| WO | 8902445 | A1 | 3/1989 |
| WO | 8908467 | A1 | 9/1989 |
| WO | 9012551 | A1 | 11/1990 |
| WO | 9206639 | A2 | 4/1992 |
| WO | 9220349 | A1 | 11/1992 |
| WO | 9310731 | A1 | 6/1993 |
| WO | 9311805 | A1 | 6/1993 |
| WO | 9318174 | A1 | 9/1993 |
| WO | 9417747 | A1 | 8/1994 |
| WO | 9507666 | A1 | 3/1995 |
| WO | 9518638 | A1 | 7/1995 |
| WO | 9532687 | A1 | 12/1995 |
| WO | 9603091 | A1 | 2/1996 |
| WO | 9608277 | A1 | 3/1996 |
| WO | 9609795 | A1 | 4/1996 |
| WO | 9614805 | A1 | 5/1996 |
| WO | 9641588 | A1 | 12/1996 |
| WO | 9735533 | A1 | 10/1997 |
| WO | 9835632 | A1 | 8/1998 |
| WO | 9849967 | A1 | 11/1998 |
| WO | 9905990 | A1 | 2/1999 |
| WO | 9906079 | A1 | 2/1999 |
| WO | 9906080 | A1 | 2/1999 |
| WO | 9951163 | A1 | 10/1999 |
| WO | 0016821 | A1 | 3/2000 |
| WO | 0067663 | A1 | 11/2000 |
| WO | 0115625 | A1 | 3/2001 |
| WO | 0180773 | A1 | 11/2001 |
| WO | 0181667 | A1 | 11/2001 |
| WO | 0185060 | A1 | 11/2001 |
| WO | 2001080773 | A1 | 11/2001 |
| WO | 2001085060 | A1 | 11/2001 |
| WO | 0207648 | A1 | 1/2002 |
| WO | 0217853 | A2 | 3/2002 |
| WO | 02078568 | A1 | 10/2002 |
| WO | 03002168 | A1 | 1/2003 |
| WO | 2004004600 | A1 | 1/2004 |
| WO | 2004071349 | A2 | 8/2004 |
| WO | 2004078120 | A2 | 9/2004 |
| WO | 2004096098 | A1 | 11/2004 |
| WO | 2004103212 | A1 | 12/2004 |
| WO | 2005011280 | A1 | 2/2005 |
| WO | 2005013863 | A2 | 2/2005 |
| WO | 2005018698 | A1 | 3/2005 |
| WO | 2005048708 | A1 | 6/2005 |
| WO | 2005105172 | A1 | 11/2005 |
| WO | 2006018552 | A1 | 2/2006 |
| WO | 2006023444 | A2 | 3/2006 |
| WO | 2006032812 | A2 | 3/2006 |
| WO | 2007004214 | A2 | 1/2007 |
| WO | 2008066883 | A2 | 6/2008 |
| WO | 2009039373 | A1 | 3/2009 |
| WO | 2009071998 | A2 | 6/2009 |
| WO | 2009031035 | A3 | 1/2010 |
| WO | 2010043978 | A2 | 4/2010 |
| WO | 2007048099 | A3 | 9/2010 |
| WO | 2011007062 | A1 | 1/2011 |
| WO | 2011026987 | A1 | 3/2011 |
| WO | 2011038740 | A1 | 4/2011 |
| WO | 2014041577 | A1 | 3/2014 |

OTHER PUBLICATIONS

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Chen, G. et al., "A Hybrid Network of Synthetic Polymer Mesh and Collagen Sponge," The Royal Society of Chemistry 2000, Chem. Commun., Jul. 2000, pp. 1505-1506.

Collins, R. et al., "Use of collagen film as a dural substitute: Preliminary animal studies," Journal of Biomedical Materials Research, Feb. 1991, pp. 267-276, vol. 25.

Dr. S. Raz, "The Karl Mayer Guide to Tehnical Textiles," Jan. 2000, pp. 1-36, Obertshausen, Germany. Best copy Available.

Extended European Search Report issued in European Patent Application No. 21170611.4 dated Oct. 7, 2021, 9 pages.

Junge, K. et al., "Functional and Morphologic Properties of a Modified Mesh for Inguinal Hernia Repair," World J. Surg., Sep. 2002, pp. 1472-1480, 26.

Klinge, U. et al., "Foreign Body Reaction to Meshes Used for the Repair of Abdominal Wall Hernias," Eur J. Surg, Sep. 1999, pp. 665-673, 165.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Langenbech, M. R. et al., "Comparison of biomaterials in the early postoperative period," Surg Endosc., May 2003, pp. 1105-1109, 17 (7).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Prokop, A. et al., "Water Soluble Polymers for Immunoisolation I: Complex Coacevation and Cytotoxicity," Advances in Polymer Science, Jul. 1998, pp. 1-51, 136.

Rao, B. et al., "Use of chitosan as a biomaterial: Studies on its safety and hemostatic potential," J. Biomed. Mater. Res., Jan. 1997, pp. 21-28, 34.

Rosen, M. et al., "Laparoscopic component separation in the single-stage treatment of infected abdominal wall prosthetic removal," Hernia, 2007, pp. 435-440, 11, published online Jul. 2007.

(56)                    References Cited

OTHER PUBLICATIONS

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).
Strand, S. et al., "Screening of Chitosans and Conditions for Bacterial Flocculation," Biomacromolecules, Mar. 2001, 126-133, 2.
Varum, K. et al., "In vitro degradation rates of partially N-acetylated chitosans in human serum," Carbohydrate Research, Mar. 1997, pp. 99-101, 299.
Welty, G. et al., "Functional impairment and complaints following incisional hernia repair with different polypropylene meshes," Hernia, Aug. 2001; pp. 142-147, 5.
Zvyagintseva, T. et al., "Inhibition of complement activation by water-soluble polysaccharides of some far-eastern brown seaweeds," Comparative Biochem and Physiol, Jul. 2000, pp. 209-215, 126(3).

* cited by examiner

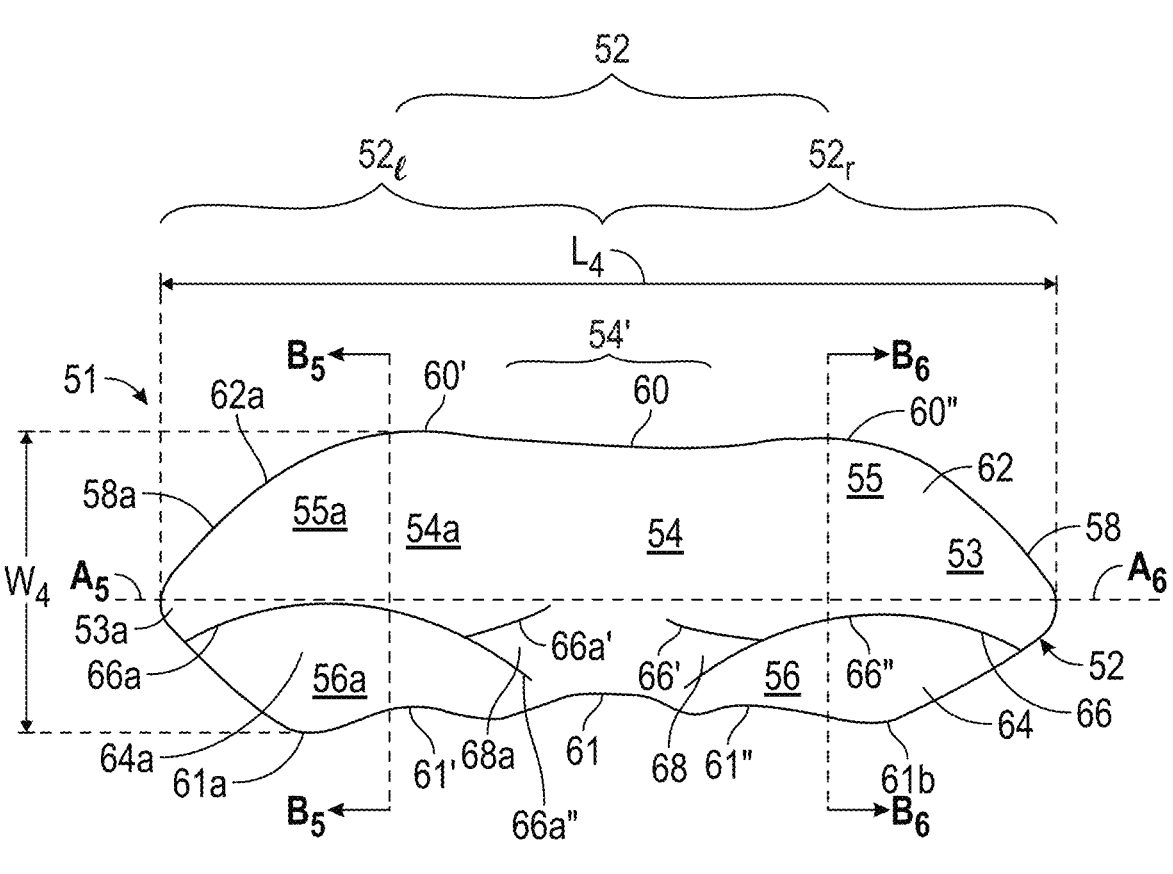
FIG. 13
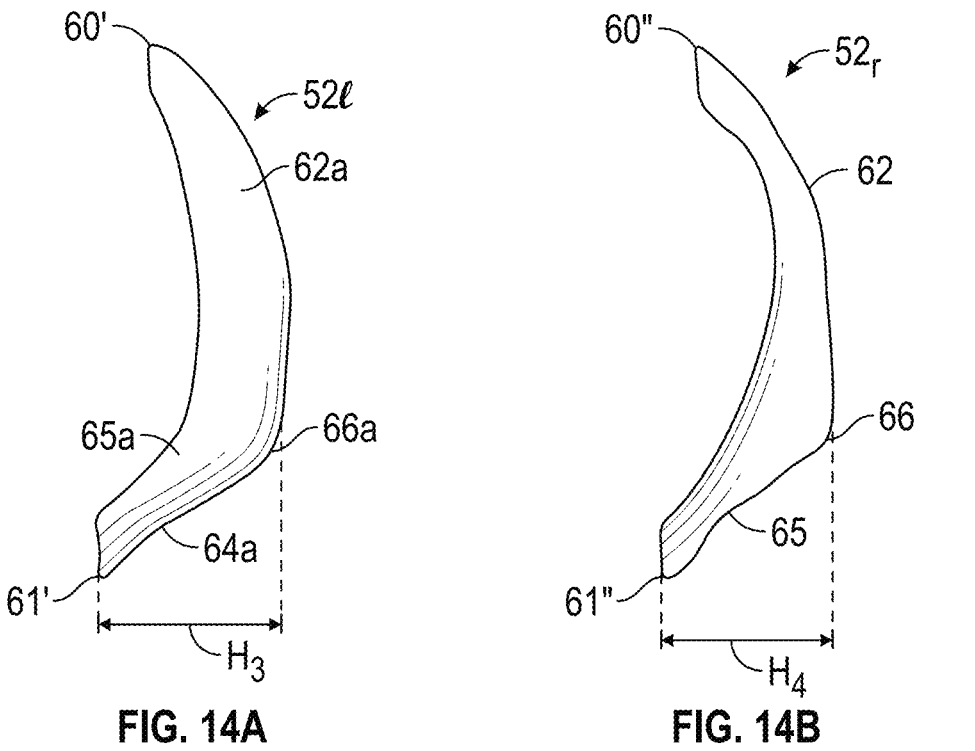
FIG. 14A          FIG. 14B

51

IMPLANTABLE PROTHESIS FOR MINIMALLY INVASIVE HERNIA REPAIR

CROSS-REFERENCE TO RELATED APPLICATIONS

This application is a continuation of U.S. patent application Ser. No. 17/238,975 filed Apr. 23, 2021, which claims the benefit of and priority to U.S. Provisional Patent Application No. 63/016,750 filed on Apr. 28, 2020, the disclosure of each of the above-identified applications is hereby incorporated by reference in its entirety.

BACKGROUND

Technical Field

The instant disclosure relates to an implantable prosthesis for use in hernia repair surgery. In particular, the implantable prosthesis can be used during minimally invasive surgical repair of inguinal hernias, including direct, indirect, and bilateral hernia defects.

Related Art

Surgically implantable prosthetic mesh patches ("prosthetic mesh," "implantable mesh," "implantable prosthesis," "mesh patch," "mesh," and/or the like) are commonly used for the repair of inguinal and other abdominal wall hernias. Currently available mesh patches designed for minimally invasive (e.g., laparoscopic or robotic) inguinal hernia repair are either flat sheets of mesh or have a three-dimensional shape that conforms to the groin anatomy. Such mesh patches typically come in three different sizes (medium, large, and extra-large), and they are generally similar in shape. Examples of currently available hernia repair mesh patches products include 3D Max™ manufactured by Bard and Dextile™ manufactured by Medtronic. These products are designed to conform to the inguinal anatomy and cover the myopectineal orifice, but they are not specifically or preferentially designed for either the direct, or indirect hernia spaces.

The foregoing discussion is intended only to illustrate the present field and should not be taken as a disavowal of claim scope.

SUMMARY

The present disclosure describes both unilateral and bilateral implantable prostheses designed for hernia repair and particularly inguinal hernia repair.

In some embodiments, an implantable prosthesis for repairing a direct or indirect inguinal hernial defect is described including a piece of biocompatible material having a preformed three-dimensional shape and defined by an outer edge. The biocompatible piece has a lateral side and an opposite medial side extending along a medial-lateral axis. The biocompatible piece also has a superior side and an opposite inferior side extending along a superior-inferior axis. The outer edge includes a convex lateral outer edge, a medial outer edge, a superior outer edge configured to widen the piece in a medial direction, and an inferior outer edge including one or more concave portions.

The piece further includes an upper portion, a lower portion, an interior edge, and a crease portion. The upper portion includes a spherical cap extending between the superior outer edge and an interior edge. The interior edge extends from the lateral side to the medial side of the piece. The interior edge includes a first and second bifurcated portion on a medial end thereof.

The lower portion extends between the interior edge and the inferior outer edge. The lower portion forms a wavy-shaped wall therebetween. The crease portion is located on the medial side of the piece between the first and second bifurcated end portions on the medial end of the interior edge.

In some embodiments, the superior outer edge may be generally linear. In some embodiments, the superior outer edge may be convex. In some embodiments, the medial outer edge may be a concave medial outer edge.

The biocompatible piece may further include a longest length and a widest width, the longest length extending between the convex lateral outer edge and the medial outer edge and the widest width located on the medial side of the piece extending between the superior outer edge and the inferior outer edge. The interior edge may extend from a portion of the convex lateral edge positioned inferior to the longest length.

The implantable prosthesis may further include one or more barbs positioned on a face of the piece. In some embodiments, the one or more barbs may be positioned on at least a portion of the medial side of the piece along the medial outer edge, positioned on at least a portion of the lower portion of the piece along the inferior outer edge, or both.

In some embodiments, an implantable prosthesis for repairing an indirect inguinal hernial defect is described including a piece of biocompatible material having a preformed three-dimensional shape and defined by an outer edge. The biocompatible piece has a lateral side and an opposite medial side extending along a medial-lateral axis and a superior side and an opposite inferior side extending along a superior-inferior axis. The outer edge includes a convex lateral outer edge, a medial outer edge, a superior outer edge including one or more concave portions, and an inferior outer edge including one or more concave portions.

The piece includes an upper portion, a lower portion, an interior edge, and a crease portion. The upper portion includes a spherical cap extending between the superior outer edge and the interior edge and extending from the lateral side to the medial side. The interior edge includes first and second bifurcated portions on a medial end thereof.

The lower portion extends between the interior edge and the inferior outer edge. The lower portion forms a wavy-shaped wall therebetween. The crease portion is located on the medial side and is defined between the first and second bifurcated end portions on the medial end of the interior edge.

The biocompatible piece may further include a longest length, a widest width, and a shortest width. The longest length extending between the convex lateral outer edge and the medial outer edge. The widest width on the lateral side of the piece extending between the superior outer edge and the inferior outer edge. The shortest width on the medial side of the piece extending between the one or more concave portions of the superior outer edge and the one or more concave portions of the inferior outer edge.

In some embodiments, the interior edge extends from a portion of the convex lateral edge positioned inferior to the longest length. In some embodiments, the interior edge is a non-linear interior edge extending along or crossing over at least a portion of the longest length. In some embodiments, at least one of the first and second bifurcated end portions of the interior edge are non-linear and/or do not extend to the medial outer edge.

The implantable prosthesis may further include one or more barbs positioned on a face of the piece. In some embodiments, the one or more barbs may be positioned on at least a portion of the medial side of the piece along the medial outer edge, positioned on at least a portion of the lower portion of the piece along the inferior outer edge, or both.

In still other embodiments, a bilateral implantable prosthesis for repairing a bilateral inguinal hernial defect is described including a piece of biocompatible material having a preformed three-dimensional shape and defined by an outer edge. The outer edge includes a first convex outer lateral edge, a second convex lateral edge opposite the first convex outer lateral edge, a superior outer edge, and an inferior outer edge opposite the superior outer edge.

The piece includes a first section and a second section. The first section includes a first lateral side opposite a first medial side extending along a first medial-lateral axis of the first section and a first superior side opposite a first inferior side extending along a first superior-inferior axis of the first section. The first section also includes a first upper portion including a spherical cap extending between a first portion of the superior outer edge and a first interior edge, the first interior edge extending from the first lateral side to the first medial side of the first section. The first interior edge may include a first and second bifurcated portion on a medial end thereof.

The first section may further include a first lower portion extending between the first interior edge and a first portion of the inferior outer edge, the first lower portion forming a first wavy-shaped wall. A first crease portion is located on the first medial portion of the first section of the piece and is defined between the first and second bifurcated portions of the first crease on the medial end of the first interior edge.

The second section includes a second lateral side opposite a second medial side extending along a second medial-lateral axis of the second section and a second superior side opposite a second inferior side extending along a second superior-inferior axis of the second section. The second section also includes a second upper portion including a spherical cap extending between a second portion of the superior outer edge and a second interior edge extending from the second lateral side to the second medial side. The second interior edge may include a third and fourth bifurcated portion on a medial end thereof.

The second section may further include a second lower portion extending between the second interior edge and a second portion of the inferior outer edge, the second lower portion forming a second wavy-shaped wall. A second crease portion is located on the second medial portion and is defined between the third and fourth bifurcated portions of the second crease.

The first and second medial sides of the first and second sections form a central band between the first and second lateral sides across a face of the piece of biocompatible material.

BRIEF DESCRIPTION OF THE DRAWINGS

The following figures are included to illustrate certain aspects of the present invention and should not be viewed as exclusive embodiments. The subject matter disclosed is capable of considerable modifications, alterations, combinations, and equivalents in form and function, as will occur to those skilled in the art and having the benefit of this disclosure.

FIG. 13 is a plan view of an embodiment of an implantable prosthesis designed for repair of a bilateral direct hernias.

FIG. 14A is a cross-sectional view of the first section of the implantable prosthesis along the superior-inferior axis $B_6$ shown in FIG. 13.

FIG. 14B is a cross-sectional view of the second section of the implantable prosthesis along the superior-inferior axis $B_6$ shown in FIG. 13.

DETAILED DESCRIPTION OF EMBODIMENTS

Figures 1, 2:
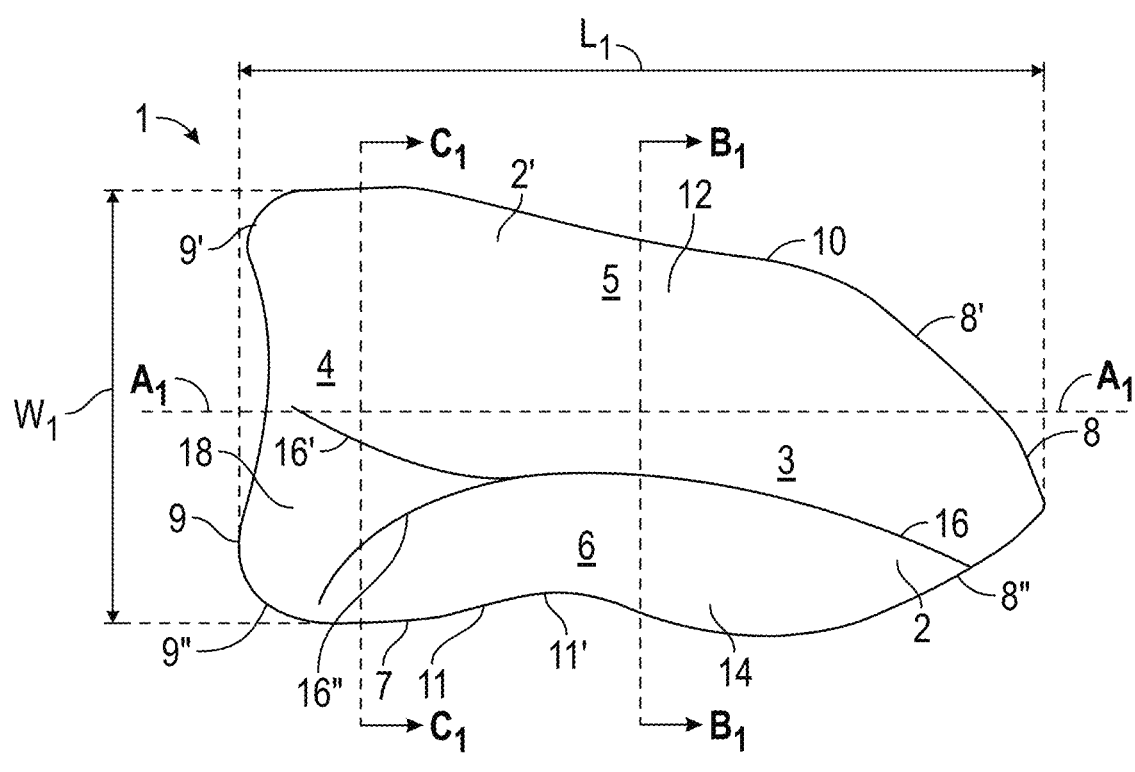
FIG. 1 is a plan view of an embodiment of an implantable prosthesis designed for repair of a right-sided direct hernia.
FIG. 2 is a cross-sectional view along the superior-inferior axis $B_1$ of the implantable prosthesis shown in FIG. 1.

Several embodiments of implantable prostheses are disclosed herein. Details of the various embodiments of the present disclosure are described below with specific reference to the figures.

FIGS. 1-19 illustrate various embodiments of an implantable prosthesis that is specifically designed for minimally invasive, robotic, or laparoscopic, repair of one or more defects in muscle or tissue wall, such as a hernia. In particular, the various embodiments of the implantable prosthesis described herein are tailored for inguinal hernia repair, including direct, indirect, and bilateral hernia defects. Direct inguinal hernias can be defined as hernias that originate through the floor of the inguinal canal, through the transversals fascia, medial to the epigastric vessels (shown and described below with respect to FIGS. 3 and 6). Indirect inguinal hernias can be defined as hernias that occur through a defect lateral to the epigastric vessels, through the internal inguinal ring (shown and described below with respect to FIGS. 9 and 12). Bilateral inguinal hernias can be defined as hernias that are present in both inguinal spaces, right and left (shown and described below with respect to FIG. 15) and can be a combination of direct and indirect hernias. For example, one side can have a direct hernia and the contralateral side can be indirect, or both can be the same type of hernia.

The implantable prostheses described herein can be made of any biocompatible material. The term biocompatible is understood as meaning that the materials can be safely implanted in the human or animal body. Biocompatible materials may include bioresorbable materials, non-bioresorbable materials, and combinations thereof.

Some non-limiting examples of bioresorbable material suitable for the piece of the prostheses described herein can be chosen from among the following materials: polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), polyethylene glycol (PE), copolymers of these materials, and mixtures thereof.

Some non-limiting examples of non-bioresorbable material suitable for the piece of the prostheses described herein can be chosen from among the following non-bioresorbable materials: polypropylenes, polyesters such as polyethylene terephthalates, polyamides, silicones, polyether ether ketone (PEEK), polyarylether ether ketone (PAEK), and mixtures thereof.

The biocompatible piece may be a porous material. In some embodiments, the biocompatible piece of material may be a surgical mesh, in particular a porous surgical mesh. The piece and/or surgical mesh may include any arrangement or assembly of biocompatible yarns, fibers, filaments and/or multifilaments, for example obtained by knitting, weaving, braiding, or even non-woven. The biocompatible pieces and/or surgical mesh, in particular porous pieces and/or surgical mesh, are suitable for the repair of a hernia defect, and particularly repair of an inguinal hernia defect.

In some embodiments, an implantable surgical mesh made of polypropylene may have a single layer monofilament weave with a large pore size (greater than about 1 mm) and a medium (standard) density between about 70-140 g/m$^2$. Further, it may be non-absorbable. The mesh can have reinforced edges (e.g., by heat sealing) to give it firmness and to avoid fraying and unraveling of the material as it is handled during the procedure.

The implantable prostheses described herein can have a variety of shapes and sizes, as further described below, and it can have a three-dimensional (3D) contour allowing them to conform to the inguinal canal anatomy (although flat contours may also be used). The prostheses can be designed to fit in the right or left inguinal space, with a specific shape that provides preferential coverage to the floor of the groin to ideally repair direct inguinal hernia defects or larger coverage laterally to provide better repair indirect inguinal hernia defects. The implantable prostheses can also cover the entire myopectineal orifice, which is the entire inguinal space from which both direct and indirect hernias occur. Further, the prostheses can be amenable to being rolled up into a cylindrical shape and inserted through a trocar or other surgical device into the abdomen or preperitoneal space. A surgeon can use a grasper tool or instrument to hold an edge of the prostheses and insert it into the appropriate body cavity by rolling it into a cylinder or scroll shape, or simply pushing it in, depending on the size of the trocar that is used for introducing the prostheses. After insertion, the prostheses can expand and return to its original 3D-conforming shape.

Figure 3:
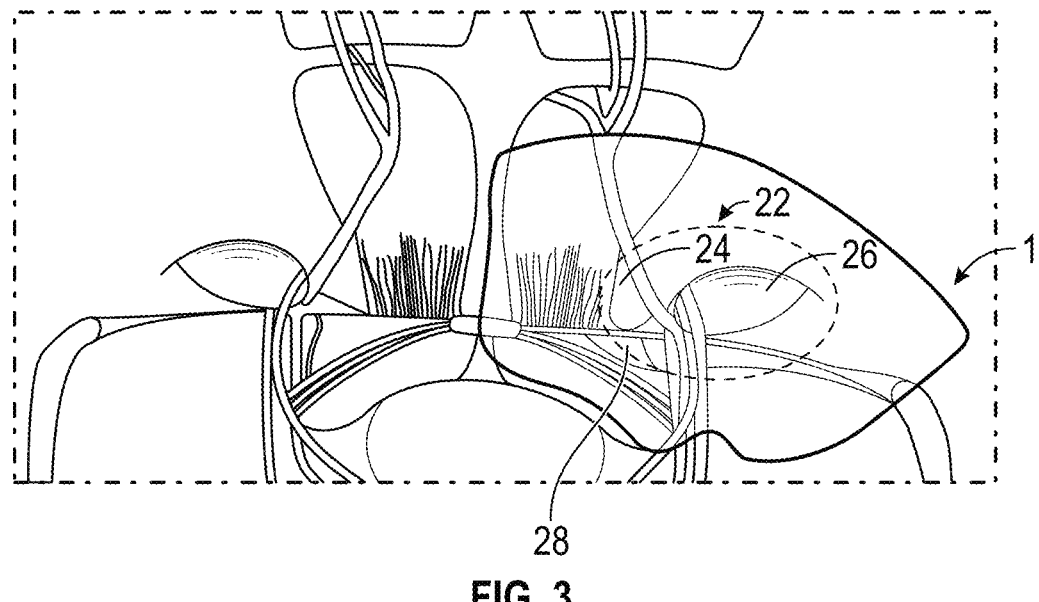
FIG. 3 is an interior view of the implantable prosthesis shown in FIG. 1 within an associated anatomical context.

Turning now to FIGS. 1-3, an implantable prosthesis 1 designed for right-sided direct hernia is shown. The implantable prosthesis 1 includes a piece 2 of biocompatible material, such as a textile or mesh, defined by an outer edge 7. The prosthesis 1 (and/or biocompatible piece 2) displays a three-dimensional shape (FIG. 2).

FIG. 1 depicts a medial-lateral axis $A_1$ and a superior-inferior axis $B_1$ across a first face 2' of the biocompatible piece 2 (and/or prosthesis 1). The biocompatible piece 2 has a lateral side 3, a medial side 4, a superior side 5, and an inferior side 6. The piece 2 also includes a second face 2" opposite the first face 2' (FIG. 2).

The outer edge 7 of the biocompatible piece 2 includes a convex lateral outer edge 8, a medial outer edge 9, a superior outer edge 10, and a concave inferior outer edge 11. The convex lateral outer edge 8 is opposite the medial outer edge 9 along the medial-lateral axis $A_1$. The superior outer edge 10 is opposite the concave inferior edge 11 along the superior-inferior axis $B_1$. The concave inferior outer edge 11 includes at least one concavity 11'. The inferior outer edge 11 connects an inferior portion 8" of the convex lateral outer edge 8 to an inferior portion 9" of the medial outer edge 9. The superior outer edge 10 connects a superior portion 8' of the convex lateral outer edge 8 to a superior portion 9' of the medial outer edge 9.

As depicted in FIG. 1, in some embodiments, the outer edge 7 of the biocompatible piece 2 includes a convex lateral outer edge 8, a concave medial outer edge 9, a concave inferior outer edge 11, and superior outer edge 10 configured to widen the piece 2 in a medial direction. In such embodiments, the widening superior outer edge 10 may be of any configuration (e.g., one or more generally linear edges, convex edges, or combinations thereof) suitable for rendering the medial side 4 of the piece 2 (and/or prosthesis 1) wider than the lateral side 3.

As further depicted in FIG. 1, in some embodiments, the biocompatible piece 2 is configured to repair a hernia, such as a direct inguinal hernia, and includes a longest length $L_1$ and a widest width $W_1$. The longest length $L_1$ extends between the convex lateral outer edge 8 and the medial outer edge 9. The widest width $W_1$ is located on the medial side 4 of the piece 2 of the prosthesis 1 designed for direct inguinal hernia repair. The widest width $W_1$ extends between the superior outer edge 10 and the wavy inferior outer edge 11.

The longest length $L_1$ of the piece 2 (and/or prosthesis 1) can be between about 14 cm and about 17 cm, and the widest width $W_1$ of the piece 2 (and/or prosthesis 1) can be between about 10 cm and about 12 cm. For example, a medium size direct hernia prosthesis 1 can be about 14 cm×10 cm ($L_1$×$W_1$). A large size direct hernia prosthesis 1 can be about 16 cm×11 cm ($L_1$×$W_1$). Finally, an extra-large size direct hernia prosthesis 1 can be 17 cm by 12 cm ($L_1$×$W_1$).

Figure 5:
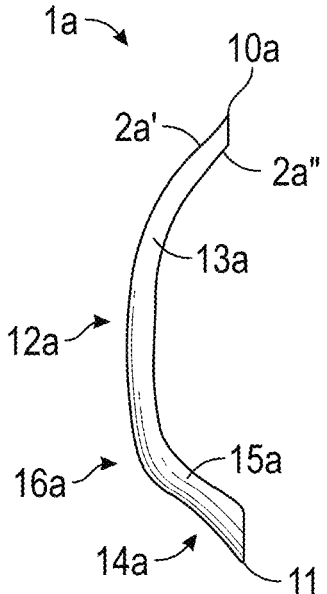
FIG. 5 is a cross-sectional view along the superior-inferior axis $B_2$ of the implantable prosthesis shown in FIG. 4.

The biocompatible piece 2 also includes an upper portion 12, a lower portion 14, an interior edge 16 extending from the lateral side 3 to the medial side 4, and a crease portion 18. The upper portion 12 extends from the lateral side 3 to the medial side 4 across at least the superior side 5 of the piece 2. The upper portion 12 also defines a curved body 13 having a height $H_1$ transverse to the length and width (FIGS. 2 and 5). The curved body 13 (and/or upper body portion 12) begins at the superior outer edge 10 and extends with a raised curved trajectory towards the interior edge 16 and to a height $H_1$ of the interior edge 16. The curved body 13 (and/or upper portion 12) may also radiate medially along the superior outer edge 10 to at least the superior portion 9' of the medial outer edge 9 and/or radiate laterally along the superior outer edge 10 to at least the superior portion 8' of the convex lateral outer edge 8. In some embodiments, the upper portion 12 may be a spherical cap.

The lower portion 14 defines a wavy-shaped wall 15 extending between the interior edge 16 and the concave inferior outer edge 11. The lower portion 14 extends between the lateral side 3, and particularly the inferior portion 8" of the convex lateral outer edge 8, to the medial side 4, and particularly the inferior portion 9" of the medial outer edge 9.

The interior edge 16 defines a crease or fold extending from the lateral side 3 to the medial side 4. As shown in FIG. 1, the interior edge 16 extends from or near a portion of the convex lateral outer edge 8 positioned inferior to the longest length $L_1$ of the piece 2. The interior edge 16 may be rounded or non-linear, as shown, extending along and/or across at least a portion of the longest length $L_1$.

The interior edge 16 includes a first and second bifurcated end portion 16', 16" on the medial side 4 of the piece 2. The first and second bifurcated end portions 16', 16" generally define the crease portion 18 therebetween, with or without a portion of the medial outer edge 9, or particularly the inferior portion 9" of the medial edge 9. In some embodiments, at least one, if not both, of the first and second bifurcated end portions 16', 16" of the interior edge 16 are rounded or non-linear. In some embodiments, at least one, if not both, of the first and second bifurcated end portions 16', 16" of the interior edge 16 may not extend to the medial outer edge 9.

The upper portion 12 of the piece 2 may have a surface area which is greater than a surface area of the lower portion 14, the crease portion 18, or both. The upper portion 12 may represent a majority of the surface area of the piece 2. In some embodiments, the upper portion 12 may represent from about 50% to about 80% of the surface area of the piece 2. In some embodiments, the upper portion 12 may represent from about 55% to about 75% of the surface area of the piece 2. In some embodiments, the upper portion 12 may represent from about 60% to about 70% of the surface area of the piece 2.

The lower portion 14 of the piece 2 may have a surface area which is less than a surface area of the upper portion 12, or greater than a surface area of the crease portion 18, or both. The lower portion 14 may represent from about 15% to about 45% of the surface area of the piece 2. In some embodiments, the lower portion 14 may represent from about 20% to about 40% of the surface area of the piece 2. In some embodiments, the lower portion 14 may represent from about 25% to about 35% of the surface area of the piece 2.

As further illustrated in FIGS. 1 and 2, the lower portion 14 of the piece 2 can have a raised, wavy section 15 designed to accommodate the iliac vessels as they course deep (posterior) to the piece 2. The first and second bifurcated end portions 16', 16" of crease 16 allows at least a portion, if not a majority, of the crease portion 18 of the piece 2 to sit in the space of Retzius, between the bladder and Cooper's ligament (shown to better advantage in FIG. 3). In addition, the curved body 13 of the upper portion 12, shown in FIG. 2, contributes to the 3D design of the prosthesis 1 and allows for an anatomical fit in the groin.

FIG. 3 illustrates the right-side direct prosthesis 1, e.g., hernia mesh, within the anatomical context in which it is designed to be implanted. The prosthesis 1 covers the right myopectineal orifice 22 (dashed line) of the groin, which includes the entire right inguinal space. The "direct" nature of the prosthesis 1 offers preferential coverage over the floor of the right inguinal canal (Hesselbach's triangle) 24, from which direct hernias originate. For example, the widest width $W_1$ of the direct prosthesis 1 is located on the medial side 4 of the prosthesis 1. Also shown in FIG. 3 is the right internal inguinal ring 26, from which indirect inguinal hernias originate, as well as the right femoral space 28, where femoral hernias can occur through the femoral canal (a space bordered by the inguinal ligament superiorly, femoral vein laterally, and Cooper's ligament inferiorly). Implantable prostheses for both direct and indirect hernias (discussed below) can also be used for the repair of femoral hernias.

The right-side direct prosthesis 1, e.g., hernia mesh, is configured to be centered over the right iliac vessels and extend medially to provide more coverage, due to its size and shape, than what is currently offered by existing implantable products. For example, the prosthesis 1 may extend medially to the symphysis pubis. The prosthesis 1 provides greater overlap over the floor of the inguinal canal, allowing for a more adequate repair of a direct inguinal hernia. The prosthesis 1 also extends laterally and is further configured to provide the required coverage of the indirect hernia space (internal inguinal ring 26) for a complete inguinal hernia repair.

Figure 4:
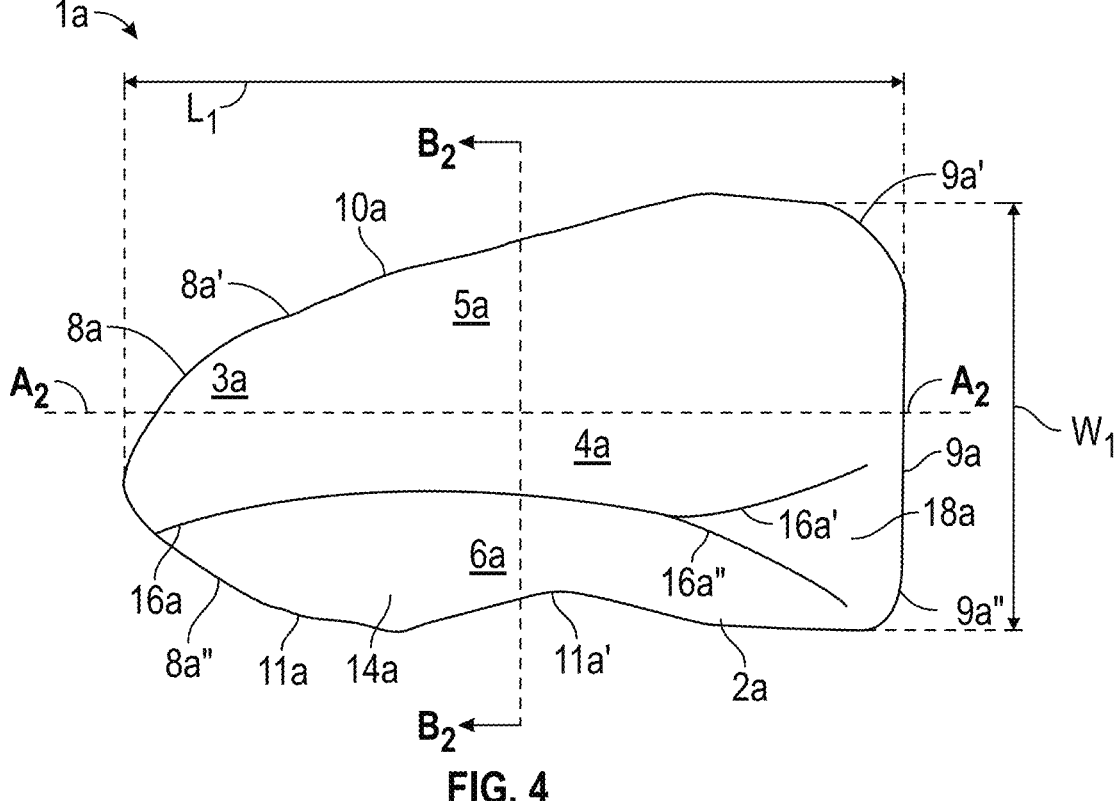
FIG. 4 is a plan view of an embodiment of an implantable prosthesis designed for repair of a left-sided direct hernia.
Figure 6:
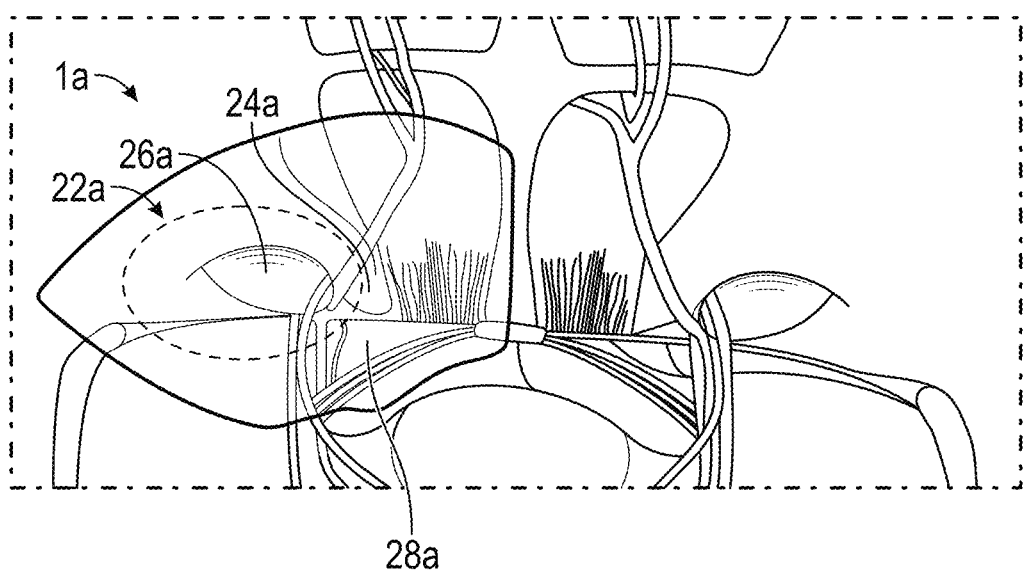
FIG. 6 is an interior view of the implantable prosthesis shown in FIG. 4 within an associated anatomical context.

Turning now to FIGS. 4-6, an embodiment of an implantable prosthesis 1a designed for a left-sided direct hernia is shown. Prosthesis 1a is largely similar to prosthesis 1, as described in detail hereinabove.

The implantable prosthesis 1a includes a piece 2a of biocompatible material, such as a textile or mesh, defined by an outer edge 7a. The prosthesis 1a (and/or biocompatible piece 2a) displays a three-dimensional shape (FIG. 5).

FIG. 4 depicts a medial-lateral axis $A_2$ and a superior-inferior axis $B_2$ across a first face 2a' of the biocompatible piece 2a (and/or prosthesis 1a). The biocompatible piece 2a has a lateral side 3a, a medial side 4a, a superior side 5a, and an inferior side 6a. The piece 2a also includes a second face 2a" opposite the first face 2a' (FIG. 5).

The outer edge 7a of the biocompatible piece 2a includes a convex lateral outer edge 8a, a medial outer edge 9a, a superior outer edge 10a, and a concave inferior outer edge 11a. The convex lateral outer edge 8a is opposite the medial outer edge 9a along the medial-lateral axis $A_2$. The superior outer edge 10a is opposite the wavy inferior edge 11a along the superior-inferior axis $B_2$. The concave inferior outer edge 11a includes at least one concavity 11a'. The inferior outer edge 11a connects an inferior portion 8a" of the convex lateral outer edge 8a to an inferior portion 9a" of the medial outer edge 9a. The superior outer edge 10a connects a superior portion 8a' of the convex lateral outer edge 8a to a superior portion 9a' of the medial outer edge 9a.

As depicted in FIG. 4, in some embodiments, the outer edge 7a of the biocompatible piece 2a includes a convex lateral outer edge 8a, a concave medial outer edge 9a, a concave inferior outer edge 11a, and superior outer edge 10a configured to widen the piece 2a in a medial direction. In such embodiments, the widening superior outer edge 10a may be of any configuration (e.g., one or more generally linear edges, convex edges, or combinations thereof) suitable for rendering the medial side $4a$ of the piece $2a$ (and/or prosthesis $1a$) wider than the lateral side $3a$.

As further depicted in FIG. 4, in some embodiments, the biocompatible piece $2a$ is configured to repair a hernia, such as a direct inguinal hernia, and includes a longest length $L_1$ and a widest width $W_1$. The longest length $L_1$ extends between the convex lateral outer edge $8a$ and the medial outer edge $9a$. The widest width $W_1$ is located on the medial side $4a$ of the piece $2a$ of the prosthesis $1a$ designed for direct inguinal hernia repair. The widest width $W_1$ extends between the superior outer edge $10a$ and the inferior outer edge $11a$.

The longest length $L_1$ of the piece $2a$ (and/or prosthesis $1_a$) can be between about 14 cm and about 17 cm, and the widest width $W_1$ of the piece $2a$ (and/or prosthesis $1_a$) can be between about 10 cm and about 12 cm. For example, a medium size direct hernia prosthesis $1_a$ can be about 14 cm×10 cm ($L_1 \times W_1$). A large size direct hernia prosthesis $1_a$ can be about 16 cm×11 cm ($L_1 \times W_1$). Finally, an extra-large size direct hernia prosthesis $1_a$ can be 17 cm by 12 cm ($L_1 \times W_1$).

The biocompatible piece $2a$ also includes an upper portion $12a$, a lower portion $14a$, an interior edge $16a$ extending from the lateral side $3a$ to the medial side $4a$, and a crease portion $18a$. The upper portion $12a$ extends from the lateral side $3a$ to the medial side $4a$ across at least the superior side $5a$ of the piece $2a$. The upper portion $12a$ also defines a curved body $13a$ (FIG. 5) having a height $H_1$ (transverse to the length and width). The curved body $13a$ (and/or upper body portion $12a$) begins at the superior outer edge $10a$ and extends with a raised curved trajectory towards the interior edge $16a$ and to a height $H_1$ of the interior edge $16a$. The curved body $13a$ (and/or upper portion $12a$) may also radiate medially along the superior outer edge $10a$ to at least the superior portion $9a'$ of the medial outer edge $9a$ and/or radiate laterally along the superior outer edge $10a$ to at least the superior portion $8a'$ of the convex lateral outer edge $8a$. In some embodiments, the upper portion $12a$ may be a spherical cap.

The lower portion $14a$ defines a wavy-shaped wall $15a$ extending between the interior edge $16a$ and the concave inferior outer edge $11a$. The lower portion $14a$ extends between the lateral side $3a$, and particularly the inferior portion $8a''$ of the convex lateral outer edge $8a$, to the medial side $4a$, and particularly the inferior portion $9a''$ of the medial outer edge $9a$.

The interior edge $16a$ defines a crease or fold extending from the lateral side $3a$ to the medial side $4a$. As shown in FIG. 4, the interior edge $16a$ extends from or near a portion of the convex lateral outer edge $8a$ positioned inferior to the longest length $L_1$ of the piece $2a$. The interior edge $16a$ may be rounded or non-linear, as shown, extending along and/or across at least a portion of the longest length $L_1$.

The interior edge $16a$ includes a first and second bifurcated end portion $16a'$, $16a''$ on the medial side $4a$ of the piece $2a$. The first and second bifurcated end portions $16a'$, $16a''$ generally define the crease portion $18a$ therebetween, with or without a portion of the medial outer edge $9a$, or particularly without the inferior portion $9a''$ of the medial edge $9a$. In some embodiments, at least one, if not both, of the first and second bifurcated end portions $16a'$, $16a''$ of the interior edge $16a$ are rounded or non-linear. In some embodiments, at least one, if not both, of the first and second bifurcated end portions $16a'$, $16a''$ of the interior edge $16a$ may not extend to the medial outer edge $9a$.

The upper portion $12a$ of the piece $2a$ may have a surface area which is greater than a surface area of the lower portion $14a$, the crease portion $18a$, or both. The upper portion $12a$ may represent a majority of the surface area of the piece $2a$. In some embodiments, the upper portion $12a$ may represent from about 50% to about 80% of the surface area of the piece $2a$. In some embodiments, the upper portion $12a$ may represent from about 55% to about 75% of the surface area of the piece $2a$. In some embodiments, the upper portion $12a$ may represent from about 60% to about 70% of the surface area of the piece $2a$.

The lower portion $14a$ of the piece $2a$ may have a surface area which is less than a surface area of the upper portion $12a$, or greater than a surface area of the crease portion $18a$, or both. The lower portion $14a$ may represent from about 15% to about 45% of the surface area of the piece $2a$. In some embodiments, the lower portion $14a$ may represent from about 20% to about 40% of the surface area of the piece $2a$. In some embodiments, the lower portion $14a$ may represent from about 25% to about 35% of the surface area of the piece $2a$.

As further illustrated in FIGS. 4 and 5, the lower portion $14a$ of the piece $2a$ can have a raised, wavy section $15a$ designed to accommodate the iliac vessels as they course deep (posterior) to the prosthesis $1a$. The first and second bifurcated end portions $16a'$, $16a''$ of crease $16a$ allows at least a portion, if not a majority, of the crease portion $18a$ of the piece $2a$ to sit in the space of Retzius, between the bladder and Cooper's ligament (shown to better advantage in FIG. 6). In addition, the curved body $13a$ of the upper portion $12a$, shown in FIG. 5, contributes to the 3D design of the piece $2a$ and allows for an anatomical fit in the groin.

FIG. 6 illustrates the left-side direct prosthesis $1a$, e.g., hernia mesh, within the anatomical context in which it is designed to be implanted. The prosthesis $1a$ covers the left myopectineal orifice $22a$ (dashed line) of the groin, which includes the entire left inguinal space. The "direct" nature of the prosthesis $1a$ offers preferential coverage over the floor of the left inguinal canal (Hesselbach's triangle) $24a$, from which direct hernias originate. For example, the widest width $W_1$ of the direct prosthesis $1a$ is located on the medial side $4a$ of the prosthesis $1a$. Also shown in FIG. 6 is the left internal inguinal ring $26a$, from which indirect inguinal hernias originate, as well as the left femoral space $28a$, where femoral hernias can occur through the femoral canal (a space bordered by the inguinal ligament superiorly, femoral vein laterally, and Cooper's ligament inferiorly). Implantable prostheses for both direct and indirect hernias (discussed below) can be used for the repair of femoral hernias.

The left-side direct prosthesis $1_a$, e.g., hernia mesh, is configured to be centered over the left iliac vessels and extend medially to provide more coverage, due to its size and shape, than what is currently offered by existing implantable products. For example, the prosthesis $1a$ may extend medially to the symphysis pubis. The prosthesis $1a$, e.g., hernia mesh, provides greater overlap over the floor of the inguinal canal, allowing for a more adequate repair of a direct inguinal hernia. The prosthesis $1a$ also extends laterally and is further configured to provide the required coverage of the indirect hernia space (internal inguinal ring $26a$) for a complete inguinal hernia repair.

Figure 7:
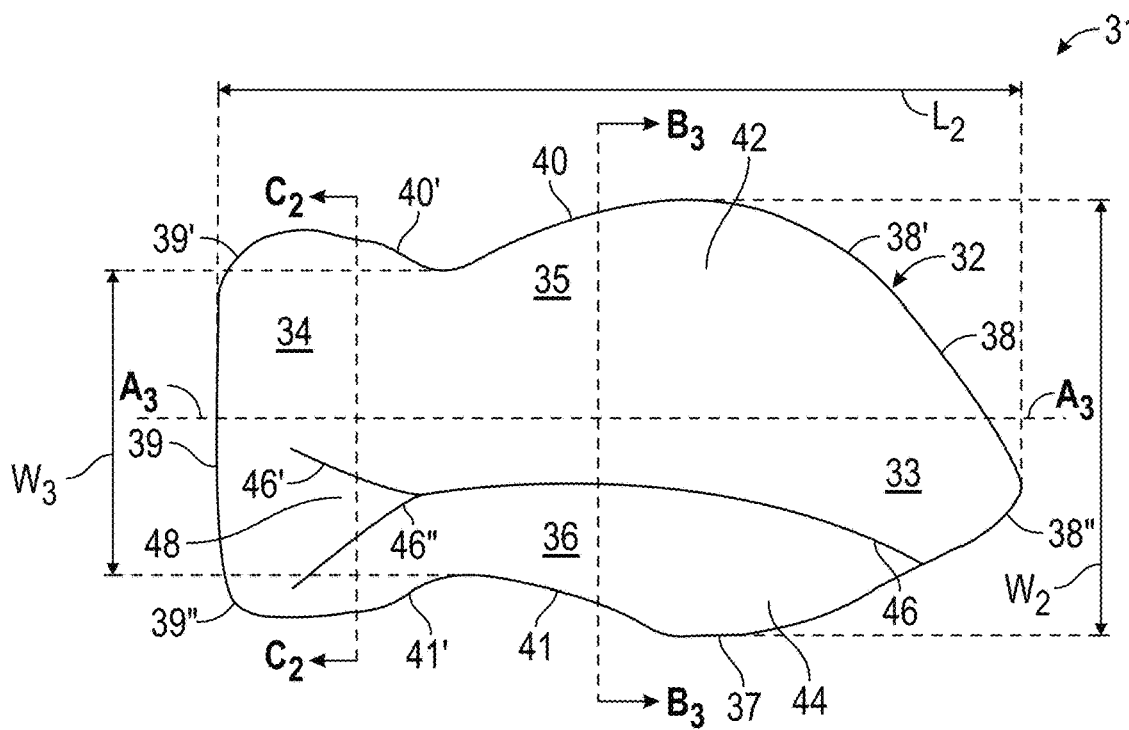
FIG. 7 is a plan view of an embodiment of an implantable prosthesis designed for repair of a right-sided indirect hernia.
Figure 8:
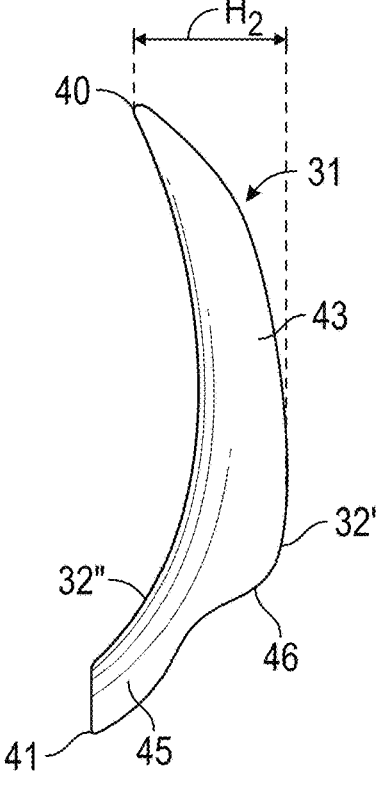
FIG. 8 is a cross-sectional view along the superior-inferior axis $B_3$ of the implantable prosthesis shown in FIG. 7.
Figure 9:
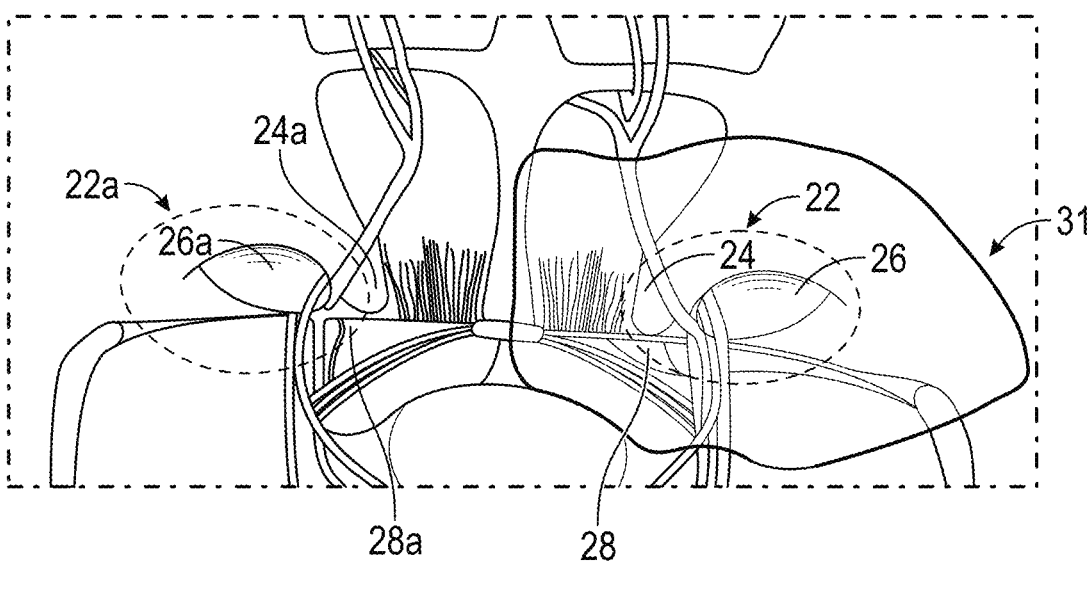
FIG. 9 is an interior view of the implantable prosthesis shown in FIG. 7 within an associated anatomical context.

Turning now to FIGS. 7-9, in some embodiments, an implantable prosthesis $31$ designed for a right-sided hernia is shown. The implantable prosthesis $31$ includes a piece $32$ of biocompatible material, such as a textile or mesh, defined by an outer edge $37$. The prosthesis $31$ (and/or biocompatible piece $32$) displays a three-dimensional shape (FIG. 8).

FIG. 7 depicts a medial-lateral axis $A_3$ and a superior-inferior axis $B_3$ across a first face 32' of the biocompatible piece 32 (and/or prosthesis 31). The biocompatible piece 32 has a lateral side 33, a medial side 34, a superior side 35, and an inferior side 36. The piece 32 also includes a second face 32" opposite the first face 32' (FIG. 8).

The outer edge 37 of the prosthesis 31 includes a convex lateral outer edge 38, a medial outer edge 39 opposite the lateral edge 38, a concave superior outer edge 40 connecting a superior portion 38' of the convex lateral outer edge 38 to a superior portion 39' of the medial outer edge 39, and a concave inferior outer edge 41 opposite the superior outer edge 40. The inferior outer edge 41 connecting an inferior portion 38" of the convex lateral outer edge 38 to an inferior portion 39" of the medial outer edge 39.

As depicted in FIG. 7, in some embodiments, the outer edge 37 of the prosthesis 31 includes a convex lateral outer edge 38, a generally linear or slightly concave medial outer edge 39, a concave superior outer edge 40, and a concave inferior outer edge 41. The concave portions 40', 41' of the superior and inferior outer edges 40, 41 are positioned on the medial side 34 of the piece 32 to create a shortest width $W_3$ between the superior and inferior outer edges 40, 41 on the medial side 34 of the piece 32.

As further depicted in FIG. 7, in some embodiments, the biocompatible piece 32 is configured to repair a hernia, such as an indirect inguinal hernia, and includes a longest length $L_2$ and a widest width $W_2$. The longest length $L_2$ extends between the convex lateral outer edge 38 and the medial outer edge 39. The widest width $W_2$ is located on the lateral side 33 of the piece 32 extending between the superior outer edge 40 and the wavy inferior outer edge 41.

The longest length $L_2$ of the prosthesis 31, e.g., surgical mesh, can be between about 14 cm and about 17 cm, and the widest width $W_2$ of the piece 32 can be between about 10 cm and about 12 cm. For example, a medium size left-side indirect hernia prosthesis 31 can be about 14 cm×10 cm ($L_2 \times W_2$). A large size left-side indirect hernia prosthesis 31 can be about 16 cm×11 cm ($L_2 \times W_2$). Finally, an extra-large size left-side indirect hernia prosthesis 31 can be 17 cm by 12 cm ($L_2 \times W_2$).

The biocompatible piece 32 includes an upper portion 42, a lower portion 44, an interior edge 46 extending from the lateral side 33 to the medial side 34, and a crease portion 48. The upper portion 42 extends from the lateral side 33 to the medial side 34 across at least the superior side 35 of the piece 32. The upper portion 42 also defines a curved body 43 (FIG. 8) having a height $H_2$ transverse to the length and width of the piece 32. The curved body 43 (and/or upper portion 42) begins at the superior outer edge 40 and extends with a raised curved trajectory towards the interior edge 46 and to a height $H_2$ of the interior edge 46. The curved body 43 (and/or upper portion 42) may also radiate medially along the superior outer edge 40 to at least the superior portion 39' of the medial outer edge 39 and/or radiate laterally along the superior outer edge 40 to at least the superior portion 38' of the convex lateral outer edge 38. In some embodiments, the upper portion 42 may be a spherical cap.

The lower portion 44 defines a wavy-shaped wall 45 extending between the interior edge 46 and the concave inferior outer edge 41. The lower portion 44 extends from the lateral side 33, and particularly from the inferior portion 38" of the convex lateral outer edge 38, to the medial side 34, and particularly not to the medial outer edge 39.

The interior edge 46 defines a crease or fold extending from the lateral side 33 to the medial side 34. As shown in FIG. 7, the interior edge 46 extends from or near a portion of the convex lateral outer edge 38 positioned inferior to the longest length $L_2$ of the piece 32. The interior edge 46 may be rounded or non-linear, as shown, extending along and/or across at least a portion of the longest length $L_2$.

The interior edge 46 includes a first and second bifurcated portion 46', 46" on the medial side 34 of the piece 32. The first and second bifurcated portions 46', 46" generally define the crease portion 48 therebetween, with or without a portion of the medial outer edge 39. In some embodiments, at least one, if not both, of the first and second bifurcated portions 46', 46" of the interior edge 46 are rounded or non-linear. In some embodiments, at least one, if not both, of the first and second bifurcated portions 46', 46" of the interior edge 46 may not extend to the medial outer edge 39.

The upper portion 42 of the piece may have a surface area which is greater than a surface area of the lower portion 44 and/or the crease portion 48. The upper portion 42 may represent a majority of the surface area of the piece 32. In some embodiments, the upper portion 42 may represent from about 50% to about 80% of the surface area of the piece 32. In some embodiments, the upper portion 42 may represent from about 55% to about 75% of the surface area of the piece 32. In some embodiments, the upper portion 42 may represent from about 60% to about 70% of the surface area of the piece 32.

As further illustrated in FIGS. 7 and 8, the lower portion 44 of the prosthesis 31 (and/or piece 32) can have a raised, wavy section 45 designed to accommodate the iliac vessels as they course deep (posterior) to the prosthesis 31. The bifurcated end portions 46', 46" of the crease 46 allows at least a portion, if not a majority, of the crease portion 48 of the prosthesis 31 to sit in the space of Retzius, between the bladder and Cooper's ligament (shown to better advantage in FIG. 9). In addition, the curved body 43, shown in FIG. 8, contributes to the 3D design of the prosthesis 31 and allows for an anatomical fit in the groin.

FIG. 9 illustrates the right-side indirect prosthesis 31, e.g., hernia mesh, within the anatomical context in which it is designed to be implanted. The prosthesis 31 covers the right myopectineal orifice 22*a* (dashed line) of the groin, which includes the entire right inguinal space. The "indirect" nature of the prosthesis 31 offers preferential coverage laterally over the right internal inguinal ring 26*a*, from which indirect inguinal hernias originate. For example, the widest width $W_2$ of the indirect prosthesis 31*a* is located on the lateral side 33 of the prosthesis 31. Also, the medial side 34 of the prosthesis 31 has the smallest width $W_3$ to reduce the amount of biocompatible material implanted while forming at least one concavity along the superior edge 40 to avoid or reduce interaction and/or irritation with the epigastric vessels 27*a*. Also shown in FIG. 9 is the right inguinal canal (Hesselbach's triangle) 24*a*, from which direct hernias originate, as well as the right femoral space 28*a*, where femoral hernias can occur through the femoral canal (a space bordered by the inguinal ligament superiorly, femoral vein laterally, and Cooper's ligament inferiorly). Implantable prostheses for both direct and indirect hernias can be used for the repair of femoral hernias.

The right-side indirect prosthesis 31, e.g., hernia mesh, is configured to be centered over the right iliac vessels and extend laterally to provide more coverage, due to its size and shape, than what is currently offered by existing prosthetic products. The prosthesis 31 provides greater overlap of the internal inguinal ring 46*a*, allowing for a more adequate repair of an indirect inguinal hernia. The prosthesis 31 also extends medially and is further configured to provide the required coverage of the direct hernia space (floor of the inguinal canal) for a complete inguinal hernia repair.

Figure 10:
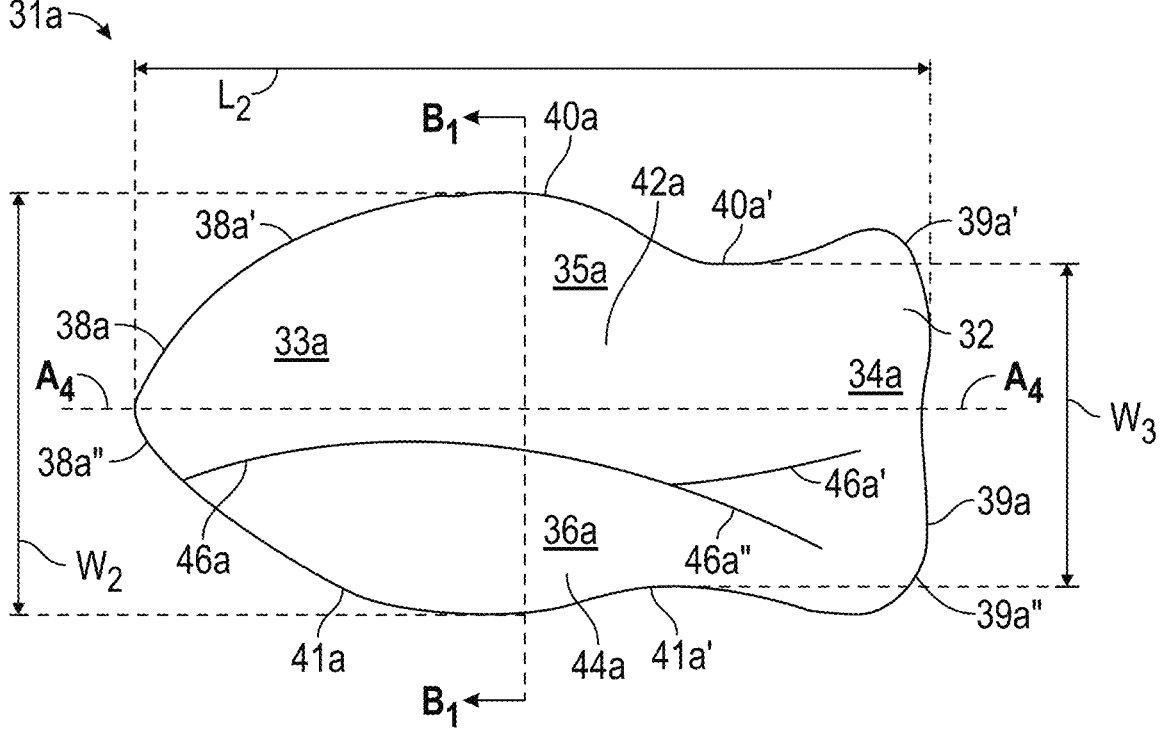
FIG. 10 is a plan view of an embodiment of an implantable prosthesis designed for repair of a left-sided indirect hernia.
Figure 11:
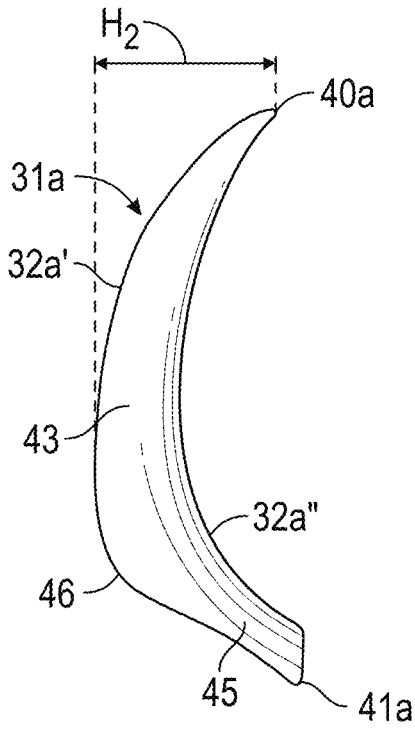
FIG. 11 is a cross-sectional view along the superior-inferior axis $B_4$ of the implantable prosthesis shown in FIG. 10.
Figure 12:
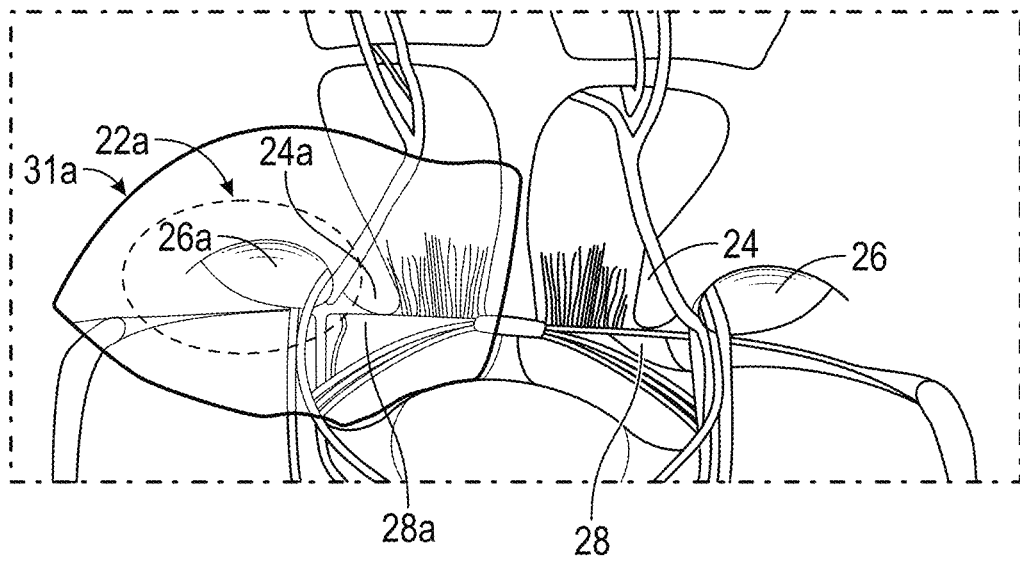
FIG. 12 is an interior view of the implantable prosthesis shown in FIG. 10 within an associated anatomical context.

Turning now to FIGS. 10-12, in some embodiments, an implantable prosthesis 31*a*, e.g., hernia mesh, is designed for a left-sided indirect hernia repair. Prosthesis 31*a* is largely similar to prosthesis 31, as described in detail hereinabove.

FIG. 10 depicts a medial-lateral axis $A_4$ and a superior-inferior axis $B_4$ across a first face 32*a'* of the biocompatible piece 32*a* (and/or prosthesis 31*a*). The biocompatible piece 32*a* has a lateral side 33*a*, a medial side 34*a*, a superior side 35*a*, and an inferior side 36*a*. The piece 32*a* also includes a second face 32*a"* opposite the first face 32*a'* (FIG. 11).

The outer edge 37*a* of the prosthesis 31*a* includes a convex lateral outer edge 38*a*, a medial outer edge 39*a* opposite the lateral edge 38*a*, a superior outer edge 40*a* connecting a superior portion 38*a'* of the convex lateral outer edge 38*a* to a superior portion 39*a'* of the medial outer edge 39*a*, and a concave inferior outer edge 41*a* opposite the superior outer edge 40*a*. The concave inferior outer edge 41*a* includes at least one concavity 41*a'*. The inferior outer edge 41*a* connecting an inferior portion 38*a"* of the convex lateral outer edge 38*a* to an inferior portion 39*a"* of the medial outer edge 39*a*.

As depicted in FIG. 10, in some embodiments, the outer edge 37*a* of the prosthesis 31*a* includes a convex lateral outer edge 38*a*, a generally linear or slightly concave medial outer edge 39*a*, a concave superior outer edge 40*a*, and a concave inferior outer edge 41*a*. The concave portions 40*a'*, 41*a'* of the superior and inferior outer edges 40*a*, 41*a* are positioned on the medial side 34*a* of the piece 32*a* to create a shortest width $W_3$ between the superior and inferior outer edges 40*a*, 41*a* on the medial side 34*a* of the piece 32*a*.

As further depicted in FIG. 10, in some embodiments, the biocompatible piece 32*a* is configured to repair a hernia, such as an indirect inguinal hernia, and includes a longest length $L_2$ and a widest width $W_2$. The longest length $L_2$ extends between the convex lateral outer edge 38*a* and the medial outer edge 39*a*. The widest width $W_2$ is located on the lateral side 33*a* of the piece 32*a* extending between the superior outer edge 40*a* and the inferior outer edge 41*a*.

The longest length $L_2$ of the prosthesis 31*a*, e.g., surgical mesh, can be between about 14 cm and about 17 cm, and the widest width $W_2$ of the prosthesis 31*a* can be between about 10 cm and about 12 cm. For example, a medium size left-side indirect hernia prosthesis 31*a* can be about 14 cm×10 cm ($L_2$×$W_2$). A large size left-side indirect hernia prosthesis 31*a* can be about 16 cm×11 cm ($L_2$×$W_2$). Finally, an extra-large size left-side indirect hernia prosthesis 31*a* can be 17 cm by 12 cm ($L_2$×$W_2$).

The biocompatible piece 32*a* includes an upper portion 42*a*, a lower portion 44*a*, an interior edge 46*a* extending from the lateral side 33*a* to the medial side 34*a*, and a crease portion 48*a*. The upper portion 42*a* extends from the lateral side 33*a* to the medial side 34*a* across at least the superior side 35*a* of the piece 32*a*. The upper portion 42*a* also defines a curved body 43*a* (FIG. 11) having a height $H_2$ transverse to the length and width of the piece 32*a*. The curved body 43*a* (and/or upper portion 42*a*) begins at the superior outer edge 40*a* and extends with a raised curved trajectory towards the interior edge 46*a* and to a height $H_2$ of the interior edge 46*a*. The curved body 43*a* (and/or upper portion 42*a*) may also radiate medially along the superior outer edge 40*a* to at least the superior portion 39*a'* of the medial outer edge 39*a* and/or radiate laterally along the superior outer edge 40*a* to at least the superior portion 38*a'* of the convex lateral outer edge 38*a*. In some embodiments, the upper portion 42*a* may be a spherical cap.

The lower portion 44*a* defines a wavy-shaped wall 45*a* extending between the interior edge 46*a* and the inferior outer edge 41*a*. The lower portion 44*a* extends from the lateral side 33*a*, and particularly from the inferior portion 38*a"* of the convex lateral outer edge 38*a*, to the medial side 34*a*, and particularly not to the medial outer edge 39*a*.

The interior edge 46*a* defines a crease or fold extending from the lateral side 33*a* to the medial side 34*a*. As shown in FIG. 10, the interior edge 46*a* extends from or near a portion of the convex lateral outer edge 38*a* positioned inferior to the longest length $L_2$ of the piece 32*a*. The interior edge 46*a* may be rounded or non-linear, as shown, extending along and/or across at least a portion of the longest length $L_2$.

The interior edge 46*a* includes a first and second bifurcated portion 46*a'*, 46*a"* on the medial side 34*a* of the piece 32*a*. The first and second bifurcated portions 46*a'*, 46*a"* generally define the crease portion 48*a* therebetween, with or without a portion of the medial outer edge 39*a*. In some embodiments, at least one, if not both, of the first and second bifurcated portions 46*a'*, 46*a"* of the interior edge 46*a* are rounded or non-linear. In some embodiments, at least one, if not both, of the first and second bifurcated portions 46*a'*, 46*a"* of the interior edge 46*a* may not extend to the medial outer edge 39*a*.

The upper portion 42*a* of the piece may have a surface area which is greater than a surface area of the lower portion 44*a* and/or the crease portion 48*a*. The upper portion 42*a* may represent a majority of the surface area of the piece 32*a*. In some embodiments, the upper portion 42*a* may represent from about 50% to about 80% of the surface area of the piece 32*a*. In some embodiments, the upper portion 42*a* may represent from about 55% to about 75% of the surface area of the piece 32*a*. In some embodiments, the upper portion 42*a* may represent from about 60% to about 70% of the surface area of the piece 32*a*.

As further illustrated in FIGS. 10 and 11, the lower portion 44 of the prosthesis 31*a* (and/or piece 32*a*) can have a raised, wavy section 45*a* designed to accommodate the iliac vessels as they course deep (posterior) to the prosthesis 31*a*. The bifurcated end portions 46*a'*, 46*a"* of the crease 46*a* allows at least a portion, if not a majority, of the crease portion 48*a* of the prosthesis 31*a* to sit in the space of Retzius, between the bladder and Cooper's ligament (shown to better advantage in FIG. 12). In addition, the curved body 43*a*, shown in FIG. 11, contributes to the 3D design of the prosthesis 31*a* and allows for an anatomical fit in the groin.

FIG. 12 illustrates the left-side indirect hernia prosthesis 31*a*, e.g., surgical mesh, within the anatomical context in which it is designed to be implanted. The prosthesis 31*a* covers the left myopectineal orifice 42*a* (dashed line) of the groin, which includes the entire left inguinal space. The "indirect" nature of the prosthesis 31*a* offers preferential coverage laterally over the left internal inguinal ring 46*a*, from which indirect inguinal hernias originate. Also shown in FIG. 12 is the left inguinal canal (Hesselbach's triangle) 44*a*, from which direct hernias originate, as well as the left femoral space 48*a*, where femoral hernias can occur through the femoral canal (a space bordered by the inguinal ligament superiorly, femoral vein laterally, and Cooper's ligament inferiorly). Implantable prostheses for both direct and indirect hernias can be used for the repair of femoral hernias.

The left-side indirect hernia prosthesis 31*a* is configured to be centered over the left iliac vessels and extend laterally to provide more coverage, due to its size and shape, than what is currently offered by existing mesh products. The prosthesis 31*a* provides greater overlap of the internal inguinal ring 46*a*, allowing for a more adequate repair of an indirect inguinal hernia. The prosthesis 31*a* also extends medially and is further configured to provide the required coverage of the direct hernia space (floor of the inguinal canal) for a complete inguinal hernia repair.

Figure 15:
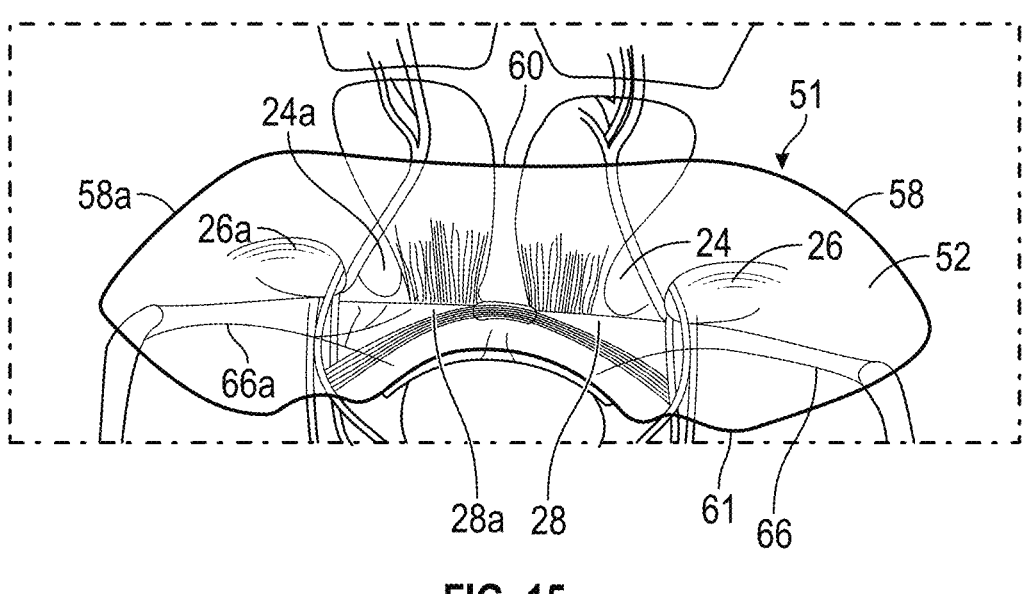
FIG. 15 is an interior view of the implantable prosthesis shown in FIG. 13 within an associated anatomical context.

Turning now to FIGS. 13-15, an embodiment of an implantable prosthesis 51 including a single biocompatible piece 52, e.g., prosthetic mesh, designed for a bilateral hernia is shown. The prosthesis 51 (and/or piece 52) is designed to anatomically cover both the right and left hernia spaces (bilateral myopectineal orifices). This single piece design allows for increased stability of the prosthesis 51, with less need for fixation and less migration of the prosthesis 51. In some embodiments, however, the prosthesis 51 may be constructed from multiple pieces attached to one another via any suitable attachment means, such as barbs, adhesives, stitching, melt-bonding, and the like. The bilateral hernia prosthesis 51 has a 3D, anatomical shape conforming to the pelvis and bilateral groins, covering bilateral myopectineal orifices as well as the space of Retzius. The bilateral hernia prosthesis 51 is configured to be inserted through a trocar and to later self-deploy back to its intended 3D shape. The bilateral hernia prosthesis 51 can be used to repair two direct, two indirect, or any combination of direct and indirect hernias.

FIG. 13 depicts an implantable prosthesis 51 including a biocompatible piece of material 52 defined by an outer edge 57 and displaying a three-dimensional shape (FIGS. 14A and 14B). The outer edge 57 includes a first convex outer lateral edge 58*a*, a second convex lateral edge 58 opposite the first convex outer lateral edge 58*a*, a superior outer edge 60, and an inferior outer edge 61 opposite the superior outer edge 60. The inferior outer edge 61 including at least one, if not two or more, concave portion 61', 61".

The biocompatible piece 52 includes a first section 52$_l$ and a second section 52$_r$ extending across the face of the piece 52. The first and second sections 52$_l$, 52$_r$ being adjacent to each other across the face of the prosthesis 51.

FIG. 13 depicts a first medial-lateral axis $A_5$ and a first superior-inferior axis $B_5$ across the first section 52$_l$ of the biocompatible piece 52 (and/or prosthesis 51) and a second medial-lateral axis $A_6$ and a second superior-inferior axis $B_6$ across the second section 52$_r$ of the biocompatible piece 52 (and/or prosthesis 51). The first and second medial-lateral axis $A_5$, $A_6$ being generally coplanar and the first and second superior-inferior axis $B_5$, $B_6$ being generally parallel to each other.

The first section 52$_l$ includes a first lateral side 53*a*, a first medial side 54*a*, a first superior side 55*a* and a first inferior side 56*a*. The second section 52$_r$ includes a second lateral side 53, a second medial side 54, a second superior side 55 and a second inferior side 56. The first medial side 54*a* of the first section 52$_l$ abuts and is attached to the second medial side 54 of the second section 52*r* to form a central band 54' of the single and/or one-piece prosthesis 51.

The first section 52$_l$ further includes a first upper portion 62*a*, a first lower portion 64*a*, a first interior edge 66*a* and a first crease portion 68*a*. The first upper portion 62*a* defines a curved body having a height $H_3$ transverse to the length and width (FIG. 14A). The first upper portion 62*a* begins at a first part 60' of the superior outer edge 60 and extends with a raised curved trajectory towards the first interior edge 66*a*. In some embodiments, the first upper portion 62*a* may be a spherical cap.

The first lower portion 64*a* extends between the first interior edge 66*a* and a first part 61*a* of the inferior outer edge 61*a*. The first lower portion 64*a* forming a first wavy-shaped wall 65*a*. The first crease portion 68*a* is defined by the first and second bifurcated end portions 66*a*', 66*a*" of the first interior edge 66*a* on the first medial side 54*a*.

The second section 52, further includes a second upper portion 62, a second lower portion 64, a second interior edge 66 and a second crease portion 68. The second upper portion 62 defines a curved body having a height $H_4$ transverse to the length and width (FIG. 14B). The second upper portion 62 begins at a second part 60" of the superior outer edge 60 and extends with a raised curved trajectory towards the second interior edge 66. In some embodiments, the second upper portion 62 may be a spherical cap.

In some embodiments, the height $H_3$ of the first section and the height $H_4$ of the second section may be equal. In some embodiments, the height $H_3$ of the first section may be greater than the height $H_4$ of the second section. In some embodiments, the height $H_3$ of the first section may be less than the height $H_4$ of the second section.

The second lower portion 64 extends between the second interior edge 66 and a second part 61*b* of the inferior outer edge 61. The second lower portion 64 forms a second wavy-shaped wall 65. The second crease portion 68 is defined by a third and fourth bifurcated end portions 66', 66" of the second interior edge 66 on the second medial side 54.

As further depicted in FIG. 13, in some embodiments, the biocompatible piece 52 is configured to repair a hernia, such as a direct inguinal hernia, and includes a longest length $L_4$ and a widest width $W_4$. The longest length $L_4$ extends between the first convex lateral outer edge 58*a* on the first section 52$_l$ of the piece 52 and the second opposite convex lateral outer edge 58 on the second section 52, of the piece 52. The widest width $W_4$ is located on the first and/or second medial side 54*a*, 54 of the first and/or second sections 52$_l$, 52$_r$.

The longest length $L_4$ of the piece 52 (and/or prosthesis 51) can be between about 28 cm and about 33 cm, and the widest width $W_4$ of the piece 52 (and/or prosthesis 51) can be between about 10 cm and about 12 cm. For example, a medium size bilateral hernia prosthesis 51 can be about 28 cm×10 cm ($L_4$×$W_4$). A large size bilateral hernia prosthesis 51 can be about 31 cm×11 cm ($L_4$×$W_4$). Finally, an extra-large size bilateral hernia prosthesis 51 can be 33 cm by 12 cm (($L_4$×$W_4$).

In some embodiments, the first interior edge 66*a* may extend from or near a portion of the first convex lateral edge 58*a* positioned inferior to the longest length $L_4$ and/or the second interior edge 66 may extend from or near a portion of the second convex lateral edge 58 positioned inferior to the longest length $L_4$.

In some embodiments, the first interior edge 66*a* may extend from or near a portion of the first convex lateral edge 58*a* positioned along the longest length $L_4$ and/or the second interior edge 66 may extend from or near a portion of the second convex lateral edge 58 along the longest length $L_4$.

As further illustrated in FIGS. 13 and 14, the first and second lower portions 64*a*, 64 of the 3D prosthesis 51 on each side can have a raised, wavy section 65*a*, 65 designed to accommodate the iliac vessels as they course deep (posterior) to the prosthesis 51. The first and second crease portions 58*a*, 58 allows the lower medial aspect of the prosthesis 51 to sit in the space of Retzius, between the bladder and Cooper's ligament (shown to better advantage in FIG. 15). In addition, the curved body 63', shown in FIG.

14, contributes to the 3D design of the prosthesis 51 and allows for an anatomical fit in the groin.

FIG. 15 illustrates the bilateral hernia prosthesis 51, e.g., surgical mesh, within the anatomical context in which it is designed to be implanted. The prosthesis 51 covers both the left and right myopectineal orifices of the groin, which includes the entire right and lefts inguinal space. The "bilateral" nature of the prosthesis 51 offers preferential coverage both medially over the floor of the inguinal canals and laterally over the internal inguinal rings. The bilateral hernia prosthesis 51 also provides coverage over the right and left femoral canals and can be used for the repair of bilateral femoral hernias.

Figure 16:
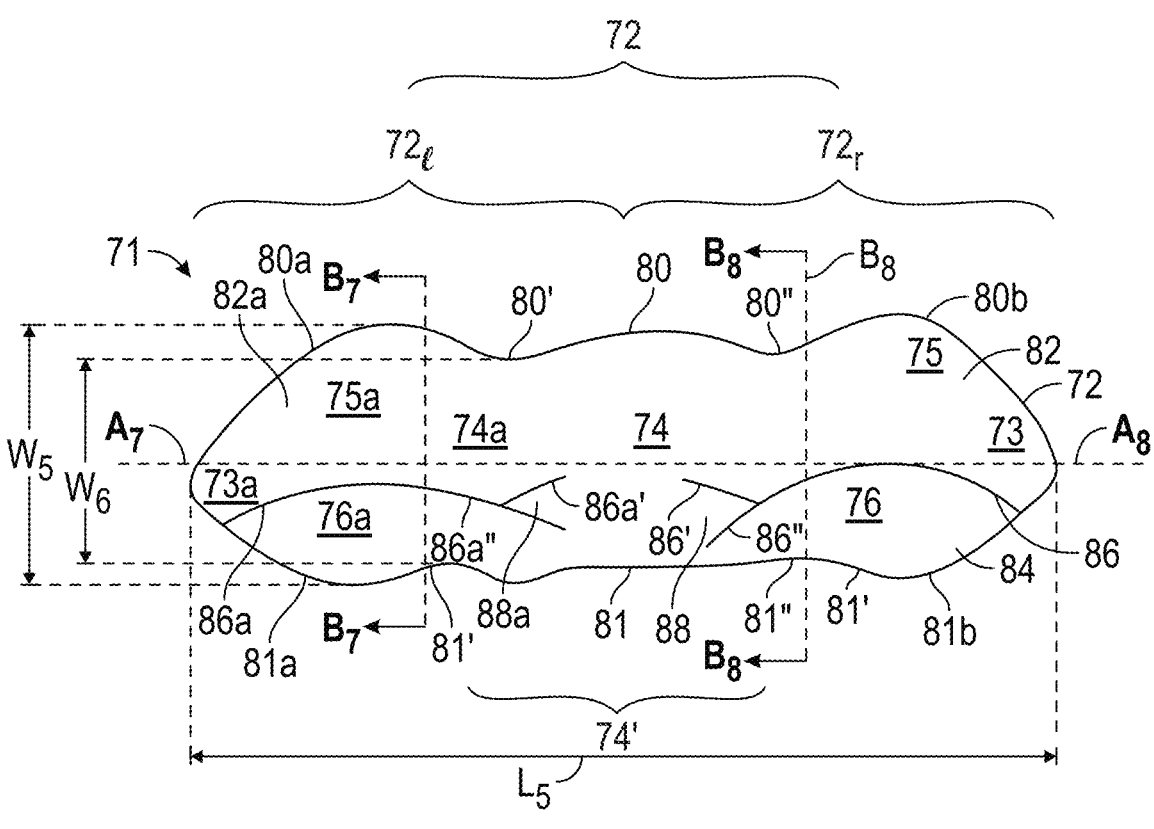
FIG. 16 is a plan view of an embodiment of an implantable prosthesis designed for repair of a bilateral indirect hernias.

Turning now to FIG. 16, an embodiment of a bilateral implantable prosthesis 71 including a single biocompatible piece 72, e.g., prosthetic mesh, designed for bilateral indirect hernias is shown. The prosthesis 71 (and/or piece 72) is designed to anatomically cover both the right and left hernia spaces (bilateral myopectineal orifices). This single piece design allows for increased stability of the prosthesis 71, with less need for fixation and less migration of the prosthesis 71. In some embodiments, however, the prosthesis 71 may be constructed from multiple pieces attached to one another via any suitable attachment means, such as barbs, adhesives, stitching, melt-bonding, and the like. The bilateral hernia prosthesis 71 has a 3D, anatomical shape conforming to the pelvis and bilateral groins, covering bilateral myopectineal orifices as well as the space of Retzius. The bilateral indirect hernia prosthesis 71 is configured to be inserted through a trocar and to later self-deploy back to its intended 3D shape. The bilateral indirect hernia prosthesis 71 can be used to repair two indirect hernias.

FIG. 16 depicts an implantable prosthesis 71 including a biocompatible piece of material 72 defined by an outer edge 77 and displaying a three-dimensional shape. The outer edge 77 includes a first convex outer lateral edge 78a, a second convex lateral edge 78 opposite the first convex outer lateral edge 78a, a superior outer edge 80, and an inferior outer edge 81 opposite the superior outer edge 80. The superior outer edge 80 includes at least one, if not two or more, concave portions 80', 80". The inferior outer edge 81 also includes at least one, if not two or more, concave portions 81', 81". In some embodiments, the concave portions of the superior outer edge are aligned with the concave portions of the inferior outer edge along a superior-inferior axis to be symmetrical.

The biocompatible piece 72 includes a first section 72ₗ and a second section 72ᵣ extending across the face of the piece 72. The first and second sections 72ₗ, 72ᵣ being adjacent to each other across the face of the prosthesis 71.

FIG. 16 depicts a first medial-lateral axis $A_7$ and a first superior-inferior axis $B_7$ across the first section 72ₗ of the biocompatible piece 72 (and/or prosthesis 71) and a second medial-lateral axis $A_8$ and a second superior-inferior axis $B_8$ across the second section 72ᵣ of the biocompatible piece 72 (and/or prosthesis 71). The first and second medial-lateral axis $A_7$, $A_8$ being generally coplanar and the first and second superior-inferior axis $B_7$, $B_8$ being generally parallel to each other.

The first section 72ₗ includes a first lateral side 73a, a first medial side 74a, a first superior side 75a and a first inferior side 76a. The second section 72ᵣ includes a second lateral side 73, a second medial side 74, a second superior side 75 and a second inferior side 76. The first medial side 74a of the first section 72ₗ abuts and is attached to the second medial side 74 of the second section 72ᵣ to form a central band 74' of the single and/or one-piece prosthesis 71.

The first section 72ₗ further includes a first upper portion 82a, a first lower portion 84a, a first interior edge 86a and a first crease portion 88a. The first upper portion 82a defines a curved body having a height $H_3$ transverse to the length and width. The first upper portion 82a begins at a first part 80a of the superior outer edge 80 and extends with a raised curved trajectory towards the first interior edge 86a. In some embodiments, the first upper portion 82a may be a spherical cap.

The first lower portion 84a extends between the first interior edge 86a and a first part 81a of the inferior outer edge 81. The first lower portion 84a forming a first wavy-shaped wall. The first crease portion 88a is defined by the first and second bifurcated end portions 86a', 86a" of the first interior edge 86a on the first medial side 74a.

The second section 72ᵣ further includes a second upper portion 82, a second lower portion 84, a second interior edge 86 and a second crease portion 88. The second upper portion 82 defines a curved body having a height $H_4$ transverse to the length and width. The second upper portion 82 begins at a second part 80b of the superior outer edge 80 and extends with a raised curved trajectory towards the second interior edge 86. In some embodiments, the second upper portion 82 may be a spherical cap.

The second lower portion 84 extends between the second interior edge 86 and a second part 81b of the inferior outer edge 81. The second lower portion 84 forms a second wavy-shaped wall. The second crease portion 88 is defined by a third and fourth bifurcated end portions 86', 86" of the second interior edge 86 on the second medial side 74.

As further depicted in FIG. 16, in some embodiments, the biocompatible piece 72 is configured to repair a hernia, such as an indirect inguinal hernia, and includes a longest length $L_5$ and a widest width $W_5$. The longest length $L_5$ extends between the first convex lateral outer edge 78a on the first section 72ₗ of the piece 72 and the second opposite convex lateral outer edge 78 on the second section 72ᵣ of the piece 72. The widest width $W_5$ is located on the first and/or second medial side 74a, 74 of the first and/or second sections 72ₗ, 72ᵣ.

The longest length $L_5$ of the piece 72 (and/or prosthesis 71) can be between about 28 cm and about 33 cm, and the widest width $W_5$ of the piece 72 (and/or prosthesis 71) can be between about 10 cm and about 12 cm. For example, a medium size bilateral hernia prosthesis 71 can be about 28 cm×10 cm ($L_5$×$W_5$). A large size bilateral hernia prosthesis 71 can be about 31 cm×11 cm ($L_5$×$W_5$). Finally, an extralarge size bilateral hernia prosthesis 71 can be 33 cm by 12 cm ($L_5$×$W_5$).

In some embodiments, the first interior edge 86a may extend from or near a portion of the first convex lateral edge 78a positioned inferior to the longest length $L_5$ and/or the second interior edge 86 may extend from or near a portion of the second convex lateral edge 78 positioned inferior to the longest length $L_5$.

In some embodiments, the first interior edge 86a may extend from or near a portion of the first convex lateral edge 78a positioned along the longest length $L_5$ and/or the second interior edge 86 may extend from or near a portion of the second convex lateral edge 78 along the longest length $L_5$.

In some embodiments, as shown in FIG. 16, a bilateral implantable prosthesis 71 may be configured to treat bilateral indirect hernias. In such embodiments, the first and second sections 72ₗ, 72ᵣ may each be configured similar h as the prostheses 31, 31a, of FIGS. 6 and 9. The bilateral indirect prosthesis 71 is defined by an outer edge 71 including a superior outer edge 80 including two or more concave edges, a wavy inferior outer edge 81 and two opposite convex lateral edges 78a, 78.

Figure 17A:
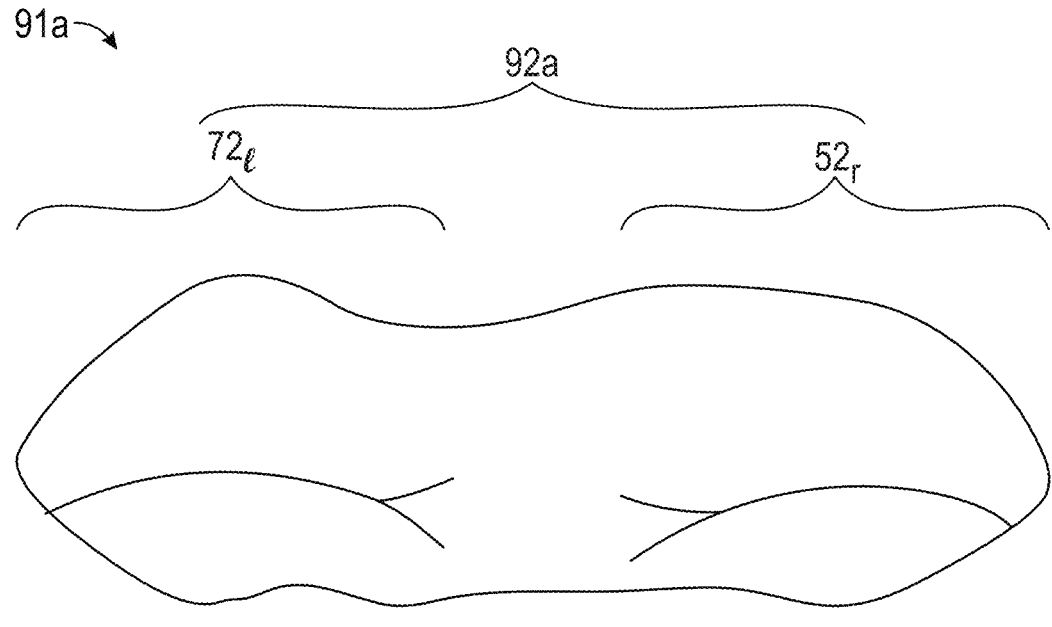
FIGS. 17A and 17B are a plan view of an embodiment of an implantable prosthesis designed for repair of a bilateral hernia including a direct and indirect hernia.

In some embodiments, as shown in FIG. 17A, a bilateral implantable prosthesis 91a configured to treat an indirect hernia and a direct hernia on opposite sides of a patient is shown. The prosthesis 91a may include a first section 72₁ configured to treat the indirect hernia (as shown and described herein with reference to FIG. 16) and a second section 52, configured to treat a direct hernia (as shown and described herein with reference to FIG. 13). Each section being largely similar to the first and second sections 72₁, 52r of FIGS. 16 and 15, respectively.

Figure 17B:
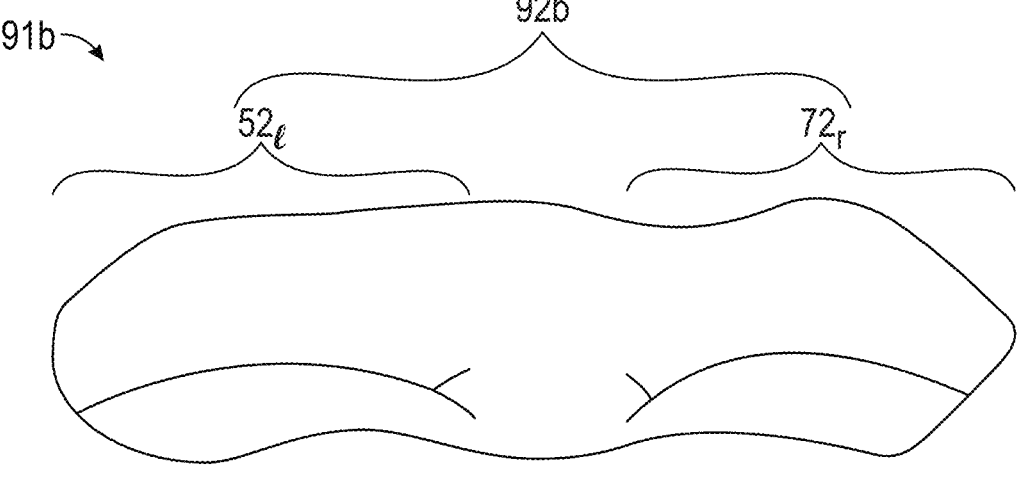

In some embodiments, as shown in FIG. 17B, a bilateral implantable prosthesis 91b configured to treat a direct hernia and an indirect hernia on opposite sides of a patient is shown. The prosthesis 91b may include a first section 52₁ configured to treat a direct hernia (as shown and described herein with reference to FIG. 13) and a second section 72 configured to treat an indirect hernia (as shown and described herein with reference to FIG. 16). Each section being largely similar to the first and second sections 52₁, 72ᵣ of FIGS. 15 and 16, respectively.

The prostheses described herein may further include a fastening means. The fastening means can be chosen from among elements that are integrally formed on the prosthesis, such as barbs, loops, and/or hooks. The fastening means designed to attach the prosthesis directly to tissue and/or to another prosthesis.

In some embodiments, the prostheses described herein may include one or more barbs. The barbs can be formed from yarns or portions of yarns that are woven and/or knitted directly with the yarns or portions of yarns used to form the prosthesis. One examples of such barbs is described in WO01/81667. Other examples for barbs, loops and hooks are also available. The one or more barbs may be positioned on any portion of the prostheses described herein.

Figure 18:
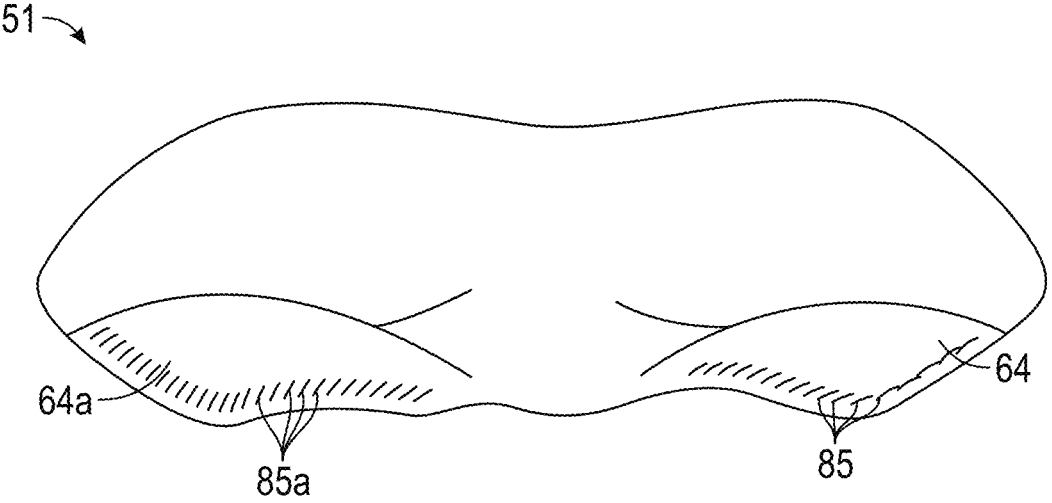
FIG. 18 is a plan view of an embodiment of a self-fastening implantable prosthesis designed for repair of a bilateral hernia.

As shown in FIG. 18, for example, in some embodiments one or more barbs 85a, 85 may be positioned on at least one, if not both, of the lower portions 64a, 64 of bilateral prosthesis 51. In other examples, the one or more barbs may be positioned on any of the lower portions 14, 14a, 44, 44a, 64, 64a, of any of the prostheses 1, 1a, 31, 31a, 51, 71, 91a, 91b (as shown in FIGS. 1, 4, 7, 10, 13, 16, 17A, 17B) described herein.

Figure 19:
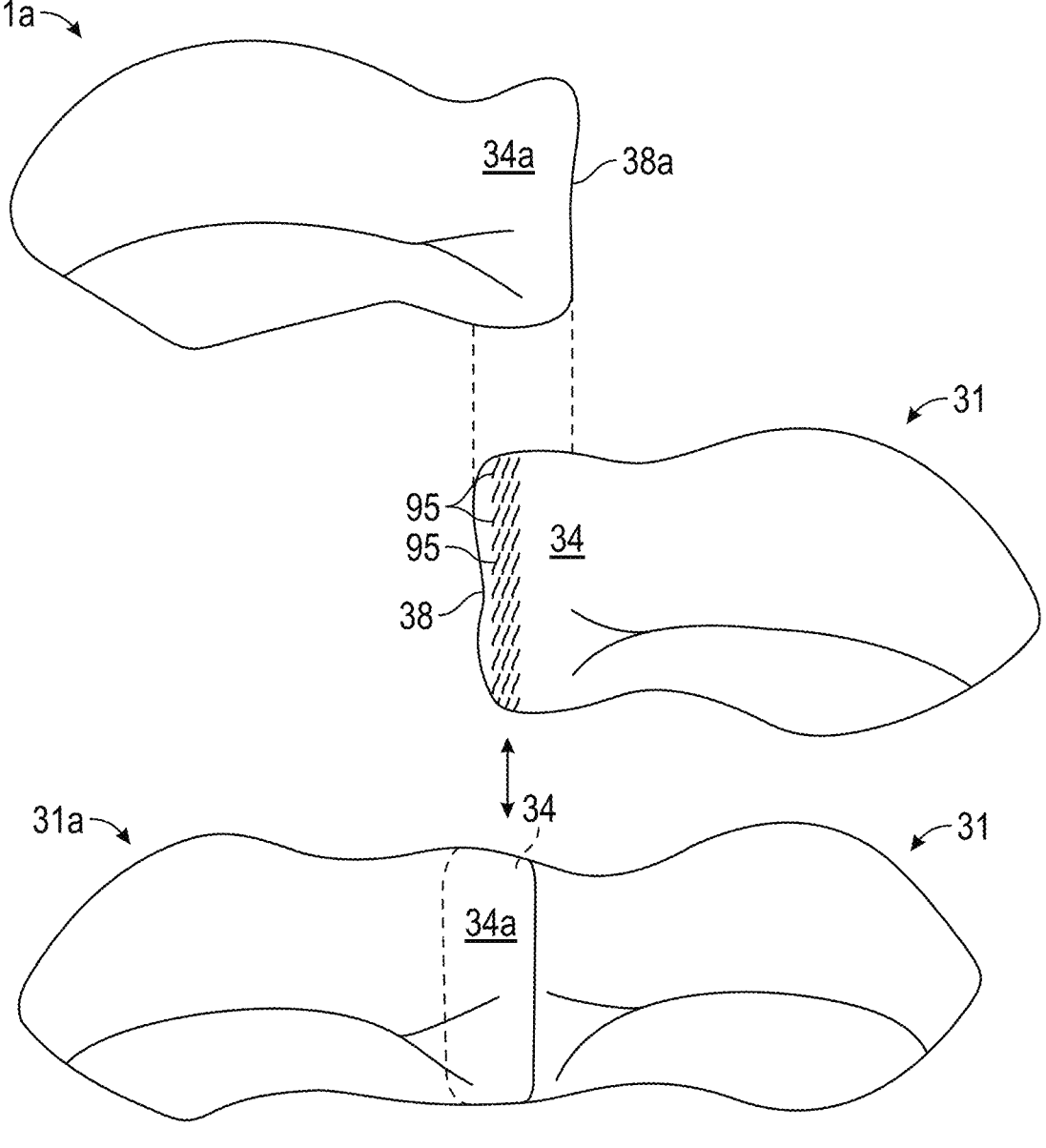
FIG. 19 is a plan view of an embodiment of a first and second unilateral implantable prosthesis being combined to form a bilateral implantable prosthesis designed for repair of a bilateral hernia.

As shown in FIG. 19, in some embodiments the one or more barbs 95 may be positioned on a first unilateral prosthesis. For example, the right-sided indirect prosthesis 31 of FIG. 7 may further include one or more barbs 95 on a medial side 34 and/or along a medial outer edge 39 thereof. In such embodiments, a second unilateral prosthesis, for example left sided indirect prosthesis 31a of FIG. 10, may be combined with the first unilateral prosthesis, e.g., right-sided indirect prosthesis 31, by overlapping the medial sides 34, 34a of each prosthesis such that the barb(s) 95 fasten the two medial sides 34, 43a of the prostheses 31, 31a to form a two-piece bilateral prosthesis. In other examples, the one or more barbs may be positioned on the medial side and/or along the medial outer edge of any of the unilateral prostheses 1, 1a, 31, 31a described herein, and combined with any other unilateral prostheses 1, 1a, 31, 31a described herein to form a two-piece bilateral prosthesis. The two-piece bilateral prosthesis maintains the ability to be separated back into two separate unilateral prostheses, if needed.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Unless explained otherwise, all technical and scientific terms used herein have the same meaning as commonly understood to one of ordinary skill in the art to which this disclosure belongs. It will be appreciated that the terms "medial" and "lateral" may be used throughout the specification with reference to portions of an implantable prosthesis. The term "medial" refers to a portion of the implantable prosthetic or the body that lies or extends toward the median axis of the body, and the term "lateral" refers to a portion of the implantable prosthetic or the body that lies or extends toward the side. It will be further appreciated that for conciseness and clarity, anatomical spatial terms such as "superior," "inferior," "anterior," and "posterior" may be used herein with respect to the illustrated embodiments. However, implantable prosthetics may be used in many orientations and positions, and these terms are not intended to be limiting and absolute.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An implantable two-piece bilateral prosthesis for repairing a bilateral inguinal hernial defect comprising:
a first unilateral prosthesis including a first piece of biocompatible material having a preformed three-dimensional shape and defined by a first outer edge, the first piece having a first lateral side and an opposite first medial side extending along a first medial-lateral axis and a first superior side and an opposite first inferior side extending along a first superior-inferior axis, and the first outer edge including a first convex lateral outer edge, a first medial outer edge, a first superior outer edge, and a first inferior outer edge including one or more first concave portions;
a second unilateral prosthesis including a second piece of biocompatible material having a preformed three-dimensional shape and defined by a second outer edge, the second piece having a second lateral side and an opposite second medial side extending along a second medial-lateral axis and a second superior side and an opposite second inferior side extending along a second superior-inferior axis, and the second outer edge including a second convex lateral outer edge, a second medial outer edge, a second superior outer edge, and a second inferior outer edge including one or more second concave portions;
one or more barbs positioned on the first medial side of the first unilateral prosthesis or the second medial side of the second unilateral prosthesis, wherein the one or more barbs are configured to fasten the first medial side of the first unilateral prosthesis to the second medial side of the second unilateral prosthesis when the first unilateral prosthesis and the second unilateral prosthesis are overlapped to form the implantable two-piece bilateral prosthesis.

2. The implantable two-piece bilateral prosthesis of claim 1, wherein the first superior outer edge is generally linear.

3. The implantable two-piece bilateral prosthesis of claim 1, wherein the first superior outer edge includes one or more concaves portions.

4. The implantable two-piece bilateral prosthesis of claim 1, wherein the first medial outer edge is a first concave medial outer edge.

5. The implantable two-piece bilateral prosthesis of claim 1, wherein the first unilateral prosthesis further includes:
a first upper portion including a first spherical cap extending between the first superior outer edge and a first interior edge extending from the first lateral side to the first medial side, the first interior edge including first and second bifurcated portions on a first medial end thereof, a first lower portion extending between the first interior edge and the first inferior outer edge, the first lower portion forming a first wavy-shaped wall, and
a first crease portion on the first medial side, the first crease portion defined between the first and second bifurcated end portions on the first medial end thereof.

6. The implantable two-piece bilateral prosthesis of claim 5, wherein at least one of the first and second bifurcated portions of the first interior edge are non-linear and do not extend to the first medial outer edge.

7. The implantable two-piece bilateral prosthesis of claim 5, wherein the first piece further includes a first longest length and a first widest width, the first longest length extending between the first convex lateral outer edge and the first medial outer edge and the first widest width located on the first medial side of the first piece extending between the first superior outer edge and the first inferior outer edge.

8. The implantable two-piece bilateral prosthesis according to claim 7, wherein the first interior edge extends from a portion of the first convex lateral edge positioned inferior to the first longest length.

9. The implantable two-piece bilateral prosthesis according to claim 7, wherein the first interior edge is a first non-linear interior edge extending along or crossing over at least a portion of the first longest length.

10. The implantable two-piece bilateral prosthesis of claim 1, wherein the second superior outer edge is generally linear.

11. The implantable two-piece bilateral prosthesis of claim 1, wherein the second superior outer edge includes one or more concaves portions.

12. The implantable two-piece bilateral prosthesis of claim 1, wherein the second medial outer edge is a second concave medial outer edge.

13. The implantable two-piece bilateral prosthesis of claim 1, wherein the second unilateral prosthesis further includes:
a second upper portion including a second spherical cap extending between the second superior outer edge and a second interior edge extending from the second lateral side to the second medial side, the second interior edge including third and fourth bifurcated portions on a second medial end thereof,
a second lower portion extending between the second interior edge and the second inferior outer edge, the second lower portion forming a second wavy-shaped wall, and
a second crease portion on the second medial side, the second crease portion defined between the third and fourth bifurcated end portions on the second medial end thereof.

14. The implantable two-piece bilateral prosthesis according to claim 13, wherein at least one of the third and fourth bifurcated portions of the second interior edge are non-linear and do not extend to the second medial outer edge.

15. The implantable two-piece bilateral prosthesis of claim 13, wherein the second piece further comprises a second longest length and a second widest width, the second longest length extending between the second convex lateral outer edge and the second medial outer edge and the second widest width located on the second medial side of the second piece extending between the second superior outer edge and the second inferior outer edge.

16. The implantable two-piece bilateral prosthesis according to claim 15, wherein the second interior edge extends from a portion of the second convex lateral edge positioned inferior to the second longest length.

17. The implantable two-piece bilateral prosthesis according to claim 15, wherein the second interior edge is a second non-linear interior edge extending along or crossing over at least a portion of the second longest length.

18. The implantable two-piece bilateral prosthesis according to claim 1, wherein the first unilateral prosthesis is configured to treat an indirect hernia on a first side of a patient and the second unilateral prosthesis is configured to treat a direct hernia or an indirect hernia on a second side of the patient.

19. The implantable two-piece bilateral prosthesis according to claim 1, wherein the first unilateral prosthesis is configured to treat a direct hernia on a first side of a patient and the second unilateral prosthesis is configured to treat a direct hernia or an indirect hernia on a second side of the patient.

\*     \*     \*     \*     \*